(12) United States Patent
Aranyi et al.

(10) Patent No.: US 8,652,152 B2
(45) Date of Patent: Feb. 18, 2014

(54) CLIP APPLYING APPARATUS AND LIGATION CLIP

(75) Inventors: Ernest Aranyi, Easton, CT (US); Kenneth H. Whitfield, New Haven, CT (US)

(73) Assignee: Covidien LP, Mansfield, MA (US)

( * ) Notice: Subject to any disclaimer, the term of this patent is extended or adjusted under 35 U.S.C. 154(b) by 845 days.

(21) Appl. No.: 11/233,541

(22) Filed: Sep. 23, 2005

(65) Prior Publication Data

US 2006/0064117 A1    Mar. 23, 2006

Related U.S. Application Data

(60) Provisional application No. 60/612,620, filed on Sep. 23, 2004.

(51) Int. Cl.
*A61B 17/10* (2006.01)

(52) U.S. Cl.
USPC .......................................................... 606/143

(58) Field of Classification Search
USPC ......... 606/143, 139, 151, 159, 142, 157, 158; 227/175.1, 176.1, 177.1, 179.1
See application file for complete search history.

(56) References Cited

U.S. PATENT DOCUMENTS

| | | | |
|---|---|---|---|
| 3,683,927 A * | 8/1972 | Noiles ............................ | 606/143 |
| 4,043,504 A | 8/1977 | Hueil et al. | |
| 4,086,926 A * | 5/1978 | Green et al. ................... | 606/143 |
| 4,169,476 A | 10/1979 | Hiltebrandt | |
| 4,246,903 A | 1/1981 | Larkin | |
| 4,375,866 A | 3/1983 | Giersch et al. | |
| 4,480,640 A | 11/1984 | Becht | |
| 4,480,641 A | 11/1984 | Failla et al. | |
| 4,487,204 A | 12/1984 | Hrouda | |
| 4,491,133 A | 1/1985 | Menges et al. | |
| 4,492,232 A | 1/1985 | Green | |
| 4,500,024 A | 2/1985 | DiGiovanni et al. | |
| 4,509,518 A | 4/1985 | McGarry et al. | |
| 4,512,345 A | 4/1985 | Green | |
| 4,532,925 A | 8/1985 | Blake, III | |
| 4,534,351 A | 8/1985 | Rothfuss et al. | |
| 4,549,544 A | 10/1985 | Favaron | |
| 4,556,058 A | 12/1985 | Green | |
| 4,557,263 A | 12/1985 | Green | |
| 4,562,839 A | 1/1986 | Blake, III et al. | |
| 4,572,183 A | 2/1986 | Juska | |
| 4,576,165 A | 3/1986 | Green et al. | |
| 4,576,166 A | 3/1986 | Montgomery et al. | |

(Continued)

FOREIGN PATENT DOCUMENTS

EP    1405601 A1    4/2004

OTHER PUBLICATIONS

International Search Report for corresponding PCT Application No. PCT/US2005/33981 (4 pages).

*Primary Examiner* — S. Thomas Hughes
*Assistant Examiner* — Julie A Szpira

(57) ABSTRACT

A clip applying apparatus is provided for applying a ligating clip to tissue. The clip applying apparatus includes, inter alia, a handle assembly, a central body portion, an anvil jaw, and a slide member movably supported in relation to the anvil jaw. The anvil jaw and the slide member are configured to define an enclosed tissue receiving area when the slide member is in an advanced position. A method is also provided for ligating tissue using the presently disclosed clip applying apparatus.

27 Claims, 21 Drawing Sheets

(56) References Cited

U.S. PATENT DOCUMENTS

| | | |
|---|---|---|
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,821,721 A | 4/1989 | Chin et al. |
| 4,850,355 A | 7/1989 | Brooks et al. |
| 4,854,317 A | 8/1989 | Braun |
| 4,929,239 A | 5/1990 | Braun |
| 4,934,364 A | 6/1990 | Green |
| 4,967,949 A | 11/1990 | Sandhaus |
| 5,026,379 A | 6/1991 | Yoon |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,156,608 A | 10/1992 | Troidl et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,207,691 A | 5/1993 | Nardella |
| 5,207,692 A | 5/1993 | Kraus et al. |
| 5,246,450 A | 9/1993 | Thornton et al. |
| 5,269,792 A | 12/1993 | Kovac et al. |
| 5,282,807 A | 2/1994 | Knoepfler |
| 5,282,808 A | 2/1994 | Kovac et al. |
| 5,290,299 A | 3/1994 | Fain et al. |
| 5,300,081 A * | 4/1994 | Young et al. ................. 606/143 |
| 5,304,183 A | 4/1994 | Gourlay et al. |
| 5,306,280 A | 4/1994 | Bregen et al. |
| 5,306,283 A | 4/1994 | Conners |
| 5,330,442 A | 7/1994 | Green et al. |
| 5,330,487 A | 7/1994 | Thornton et al. |
| 5,340,360 A | 8/1994 | Stefanchik |
| 5,354,304 A | 10/1994 | Allen et al. |
| 5,366,458 A | 11/1994 | Korthoff et al. |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,991 A | 1/1995 | Brocke et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,474,567 A | 12/1995 | Stefanchik et al. |
| 5,497,933 A | 3/1996 | DeFonzo et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A * | 6/1996 | Green et al. ................. 606/143 |
| 5,527,320 A | 6/1996 | Carruthers et al. |
| 5,542,949 A | 8/1996 | Yoon |
| 5,547,474 A * | 8/1996 | Kloeckl et al. ................. 606/143 |
| 5,582,615 A | 12/1996 | Foshee et al. |
| 5,591,178 A | 1/1997 | Green et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,553 A | 7/1997 | Kolesa et al. |
| 5,649,937 A | 7/1997 | Bito et al. |
| 5,662,676 A | 9/1997 | Koninckx |
| 5,665,097 A | 9/1997 | Baker et al. |
| 5,681,330 A | 10/1997 | Hughett et al. |
| 5,695,502 A | 12/1997 | Pier et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,720,756 A | 2/1998 | Green et al. |
| 5,725,537 A | 3/1998 | Green et al. |
| 5,725,538 A | 3/1998 | Green et al. |
| 5,725,542 A | 3/1998 | Yoon |
| 5,755,726 A | 5/1998 | Pratt et al. |
| 5,769,857 A | 6/1998 | Reztzov et al. |
| 5,772,673 A | 6/1998 | Cuny et al. |
| 5,779,718 A | 7/1998 | Green et al. |
| 5,782,844 A | 7/1998 | Yoon et al. |
| 5,788,698 A | 8/1998 | Savornin |
| 5,788,716 A * | 8/1998 | Kobren et al. ................. 606/141 |
| 5,792,149 A | 8/1998 | Sherts et al. |
| 5,792,150 A | 8/1998 | Pratt et al. |
| 5,824,547 A | 10/1998 | Hashino et al. |
| 5,824,548 A | 10/1998 | Hearn |
| 5,833,695 A | 11/1998 | Yoon |
| 5,833,696 A | 11/1998 | Whitfield et al. |
| 5,835,199 A | 11/1998 | Phillips et al. |
| 5,843,097 A | 12/1998 | Mayenberger et al. |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |

(56) References Cited

U.S. PATENT DOCUMENTS

| | | | |
|---|---|---|---|
| 5,897,565 A | 4/1999 | Foster | |
| 5,904,693 A | 5/1999 | Dicesare et al. | |
| 5,921,996 A | 7/1999 | Sherman | |
| 5,928,251 A | 7/1999 | Aranyi et al. | |
| 5,938,667 A | 8/1999 | Peyser et al. | |
| 5,951,574 A | 9/1999 | Stefanchik et al. | |
| 5,972,003 A | 10/1999 | Rousseau et al. | |
| 5,976,159 A | 11/1999 | Bolduc et al. | |
| 5,993,465 A | 11/1999 | Shipp et al. | |
| 6,004,335 A | 12/1999 | Vaitekunas et al. | |
| 6,017,358 A | 1/2000 | Yoon et al. | |
| RE36,720 E | 5/2000 | Green et al. | |
| 6,059,799 A | 5/2000 | Aranyi et al. | |
| 6,099,536 A | 8/2000 | Petillo | |
| 6,099,537 A | 8/2000 | Sugai et al. | |
| 6,139,555 A | 10/2000 | Hart et al. | |
| 6,210,418 B1 | 4/2001 | Storz et al. | |
| 6,241,740 B1 | 6/2001 | Davis et al. | |
| 6,258,105 B1 | 7/2001 | Hart et al. | |
| 6,273,898 B1 | 8/2001 | Kienzle et al. | |
| 6,277,131 B1 | 8/2001 | Kalikow | |
| 6,306,149 B1 | 10/2001 | Meade | |
| 6,322,571 B1 | 11/2001 | Adams | |
| 6,350,269 B1 | 2/2002 | Shipp et al. | |
| 6,352,541 B1 | 3/2002 | Kienzle et al. | |
| 6,391,035 B1 | 5/2002 | Appleby et al. | |
| 6,423,079 B1 | 7/2002 | Blake, III | |
| 6,428,548 B1 | 8/2002 | Durgin et al. | |
| 6,440,144 B1 | 8/2002 | Bacher | |
| 6,461,363 B1 | 10/2002 | Gadberry et al. | |
| 6,494,886 B1 | 12/2002 | Wilk et al. | |
| 6,520,972 B2 | 2/2003 | Peters | |
| 6,527,786 B1 | 3/2003 | Davis et al. | |
| 6,537,289 B1 | 3/2003 | Kayan et al. | |
| 6,551,333 B2 | 4/2003 | Kuhns et al. | |
| 6,569,171 B2 | 5/2003 | DeGuillebon et al. | |
| 6,599,298 B1 | 7/2003 | Forster et al. | |
| 6,607,540 B1 | 8/2003 | Shipp | |
| 6,648,898 B1 | 11/2003 | Baxter | |
| 6,652,539 B2 | 11/2003 | Shipp et al. | |
| 6,673,083 B1 | 1/2004 | Kayan et al. | |
| 6,679,894 B2 | 1/2004 | Damarati | |
| RE38,445 E | 2/2004 | Pistl et al. | |
| 6,695,854 B1 | 2/2004 | Kayan et al. | |
| 6,743,240 B2 | 6/2004 | Smith et al. | |
| 6,773,438 B1 | 8/2004 | Knodel et al. | |
| 6,776,783 B1 | 8/2004 | Frantzen et al. | |
| 6,776,784 B2 | 8/2004 | Ginn | |
| 6,780,195 B2 | 8/2004 | Porat | |
| 6,793,666 B2 | 9/2004 | Kenifel et al. | |
| 6,802,848 B2 | 10/2004 | Anderson et al. | |
| 6,814,742 B2 | 11/2004 | Kimura et al. | |
| 6,818,009 B2 | 11/2004 | Hart et al. | |
| 6,821,273 B2 | 11/2004 | Mollenauer | |
| 6,821,284 B2 | 11/2004 | Sturtz et al. | |
| 6,835,200 B2 | 12/2004 | Laufer et al. | |
| 6,837,893 B2 | 1/2005 | Miller | |
| 6,837,894 B2 | 1/2005 | Pugsley, Jr. et al. | |
| 6,837,895 B2 | 1/2005 | Mayenberger | |
| 6,840,945 B2 | 1/2005 | Manetakis et al. | |
| 6,843,794 B2 | 1/2005 | Sixto et al. | |
| 6,849,078 B2 | 2/2005 | Durgin et al. | |
| 6,849,079 B1 | 2/2005 | Blake, III et al. | |
| 6,869,435 B2 | 3/2005 | Blake, III | |
| 6,869,436 B2 | 3/2005 | Wendlandt | |
| 6,889,116 B2 | 5/2005 | Jinno | |
| 6,896,682 B1 | 5/2005 | McClellan et al. | |
| 6,911,033 B2 | 6/2005 | De Guillebon et al. | |
| 6,913,607 B2 | 7/2005 | Ainsworth et al. | |
| 6,916,327 B2 | 7/2005 | Northrup et al. | |
| 6,923,818 B2 | 8/2005 | Muramatsu et al. | |
| 6,939,356 B2 | 9/2005 | Debbas | |
| 6,942,674 B2 | 9/2005 | Belef et al. | |
| 6,942,676 B2 | 9/2005 | Buelna | |
| 6,945,978 B1 | 9/2005 | Hyde | |
| 6,945,979 B2 | 9/2005 | Kortenbach et al. | |
| 6,949,107 B2 | 9/2005 | McGuckin et al. | |
| 6,953,465 B2 | 10/2005 | Dieck et al. | |
| 6,955,643 B2 | 10/2005 | Gellman et al. | |
| 6,959,852 B2 | 11/2005 | Shelton, IV et al. | |
| 6,960,218 B2 | 11/2005 | Rennich | |
| 6,960,221 B2 | 11/2005 | Ho et al. | |
| 6,962,594 B1 | 11/2005 | Thevenet | |
| 6,963,792 B1 | 11/2005 | Green | |
| 6,964,363 B2 | 11/2005 | Wales et al. | |
| 6,964,668 B2 | 11/2005 | Modesitt et al. | |
| 6,966,875 B1 | 11/2005 | Longobardi | |
| 6,966,917 B1 | 11/2005 | Suyker et al. | |
| 6,966,919 B2 | 11/2005 | Sixto et al. | |
| 6,966,981 B2 | 11/2005 | Binder et al. | |
| 6,969,391 B1 | 11/2005 | Gazzani | |
| 6,972,023 B2 | 12/2005 | Whayne et al. | |
| 6,972,027 B2 | 12/2005 | Fallin et al. | |
| 6,973,770 B2 | 12/2005 | Schnipke et al. | |
| 6,974,446 B2 | 12/2005 | Hommann et al. | |
| 6,974,462 B2 | 12/2005 | Sater | |
| 6,974,475 B1 | 12/2005 | Wall | |
| 6,981,505 B2 | 1/2006 | Krause et al. | |
| 6,981,628 B2 | 1/2006 | Wales | |
| 6,991,597 B2 | 1/2006 | Gellman et al. | |
| 6,991,634 B2 | 1/2006 | Sugiyama et al. | |
| 6,991,635 B2 | 1/2006 | Takamoto et al. | |
| 7,343,920 B2 * | 3/2008 | Toby et al. | 128/898 |
| 2002/0198537 A1 | 12/2002 | Smith et al. | |
| 2004/0097971 A1 | 5/2004 | Hughett | |
| 2004/0133215 A1 | 7/2004 | Baxter | |
| 2005/0119677 A1 | 6/2005 | Shipp | |
| 2005/0125010 A1 | 6/2005 | Smith et al. | |
| 2005/0149063 A1 | 7/2005 | Young et al. | |
| 2005/0171560 A1 | 8/2005 | Hughett | |
| 2005/0177176 A1 | 8/2005 | Gerbi et al. | |
| 2005/0177177 A1 | 8/2005 | Viola | |
| 2005/0216036 A1 | 9/2005 | Nakao | |
| 2005/0222588 A1 | 10/2005 | Vandenbroek et al. | |
| 2005/0222590 A1 | 10/2005 | Gadberry et al. | |
| 2005/0234478 A1 | 10/2005 | Wixey et al. | |
| 2005/0256529 A1 | 11/2005 | Yawata et al. | |
| 2005/0267495 A1 | 12/2005 | Ginn et al. | |
| 2005/0277951 A1 | 12/2005 | Smith et al. | |
| 2005/0277952 A1 | 12/2005 | Arp et al. | |
| 2005/0277953 A1 | 12/2005 | Francese et al. | |
| 2005/0277954 A1 | 12/2005 | Smith et al. | |
| 2005/0277955 A1 | 12/2005 | Palmer et al. | |
| 2005/0277956 A1 | 12/2005 | Francese et al. | |
| 2005/0277958 A1 | 12/2005 | Levinson | |
| 2005/0288689 A1 | 12/2005 | Kammerer et al. | |
| 2005/0288690 A1 | 12/2005 | Bourque et al. | |
| 2006/0004388 A1 | 1/2006 | Whayne et al. | |
| 2006/0004390 A1 | 1/2006 | Rosenberg et al. | |
| 2006/0009789 A1 | 1/2006 | Gambale et al. | |
| 2006/0009790 A1 | 1/2006 | Blake, III et al. | |
| 2006/0009792 A1 | 1/2006 | Baker et al. | |
| 2006/0020270 A1 | 1/2006 | Jabba et al. | |
| 2006/0020271 A1 | 1/2006 | Stewart et al. | |

\* cited by examiner

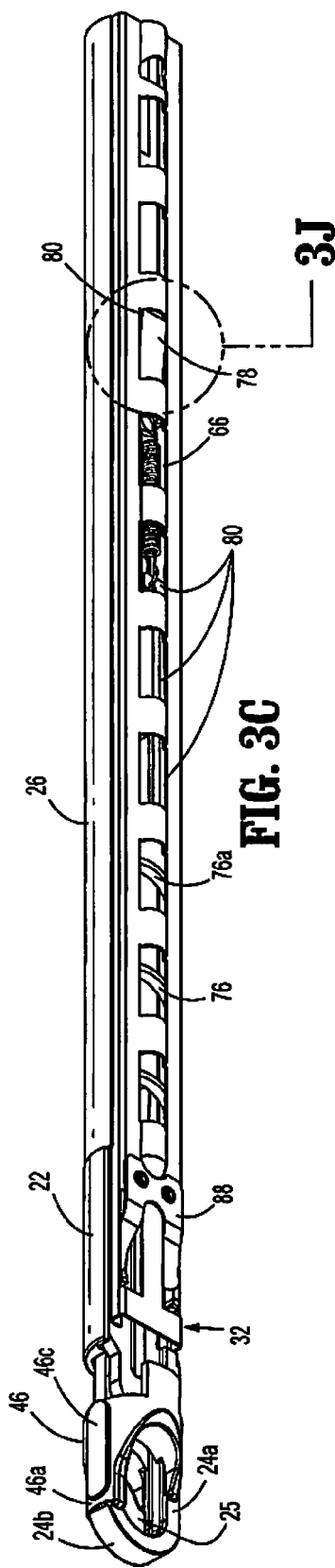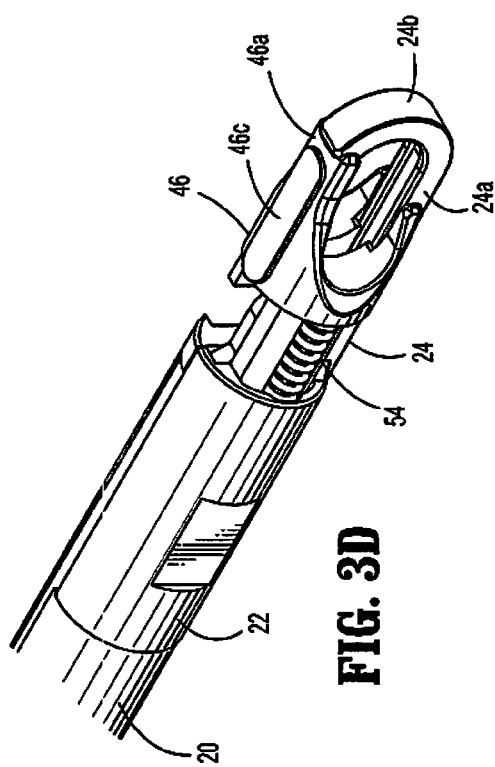

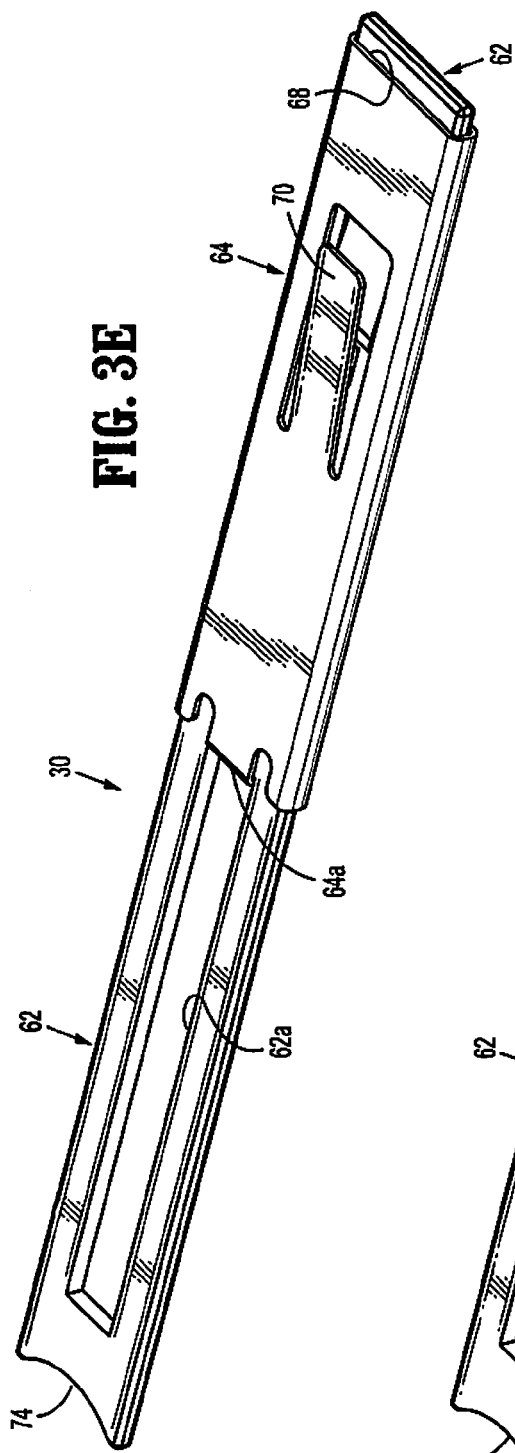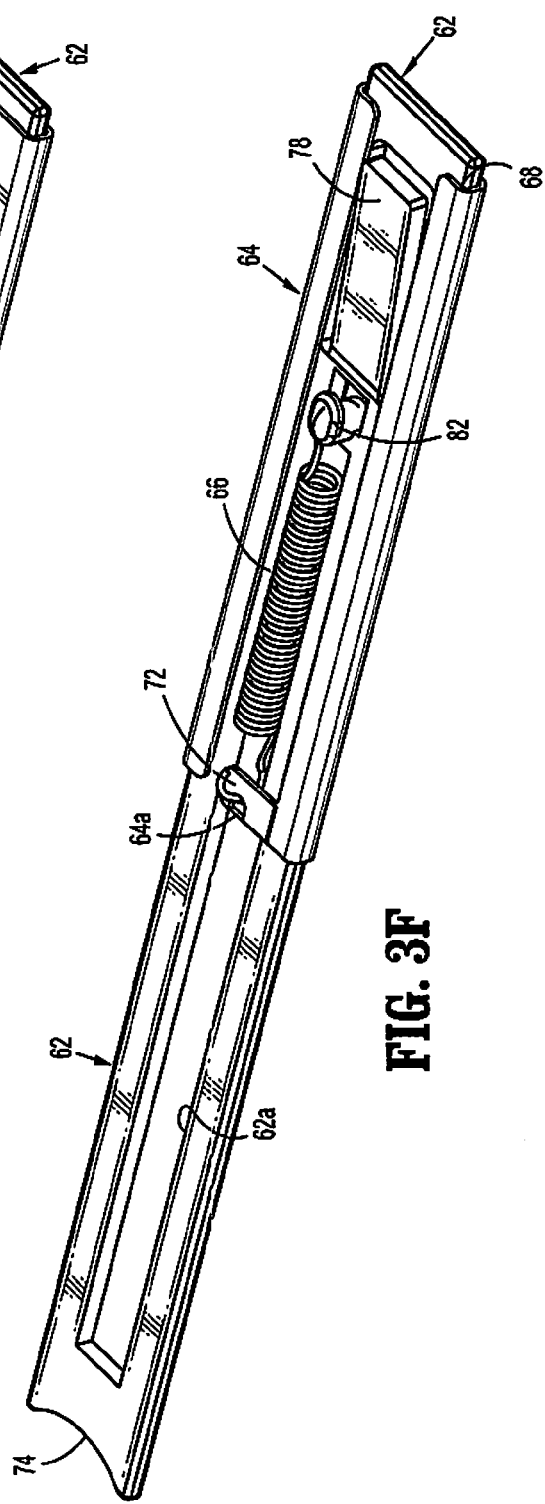

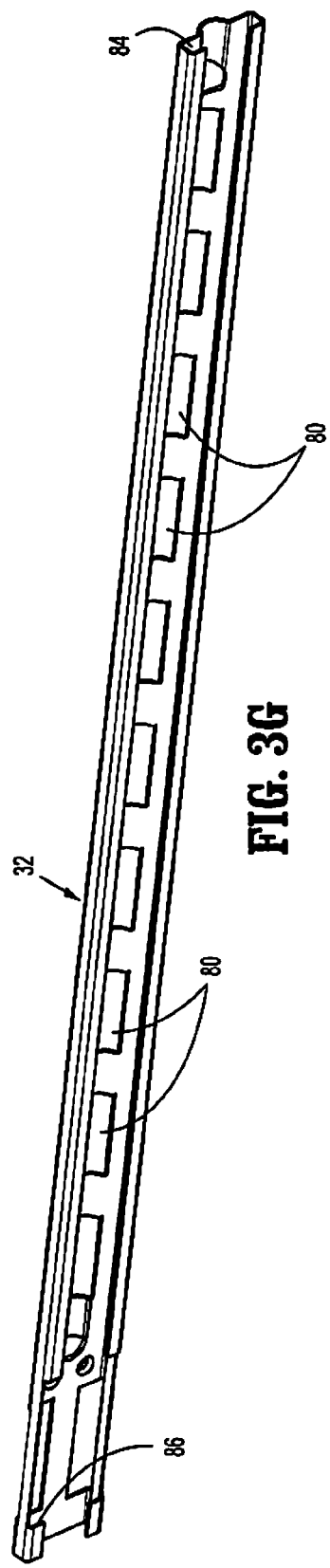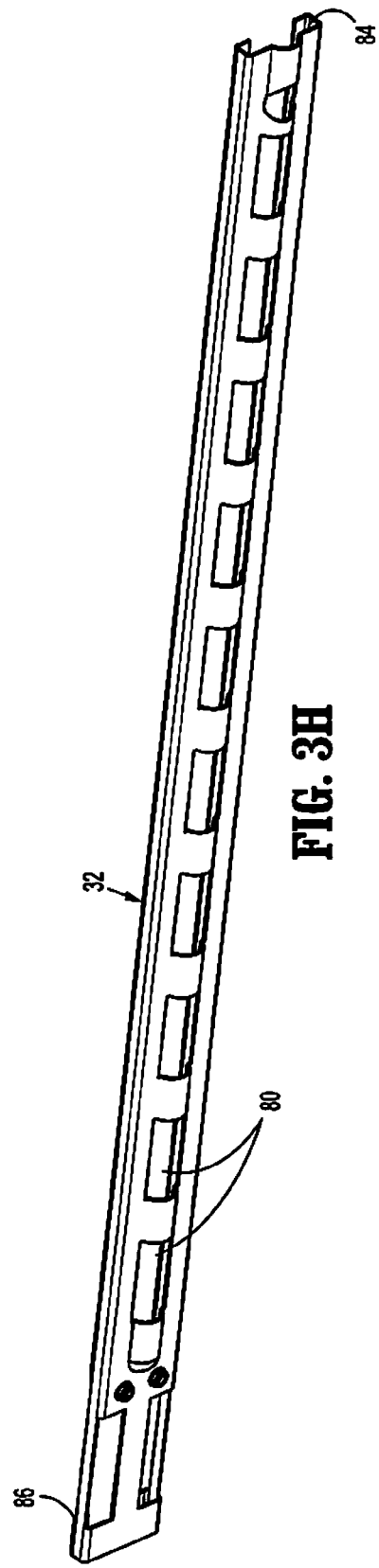

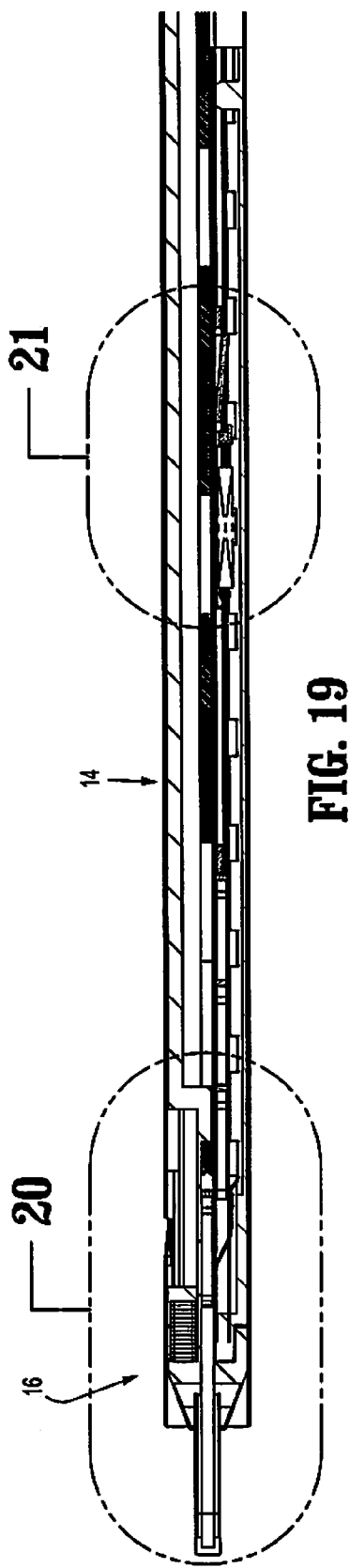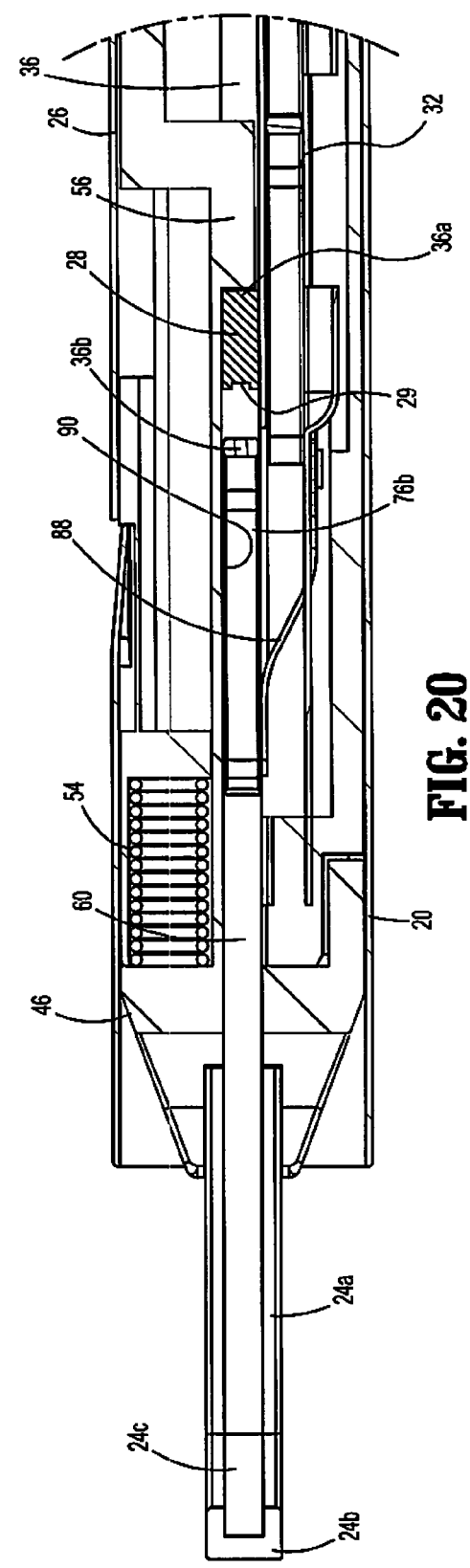
FIG. 19
FIG. 20

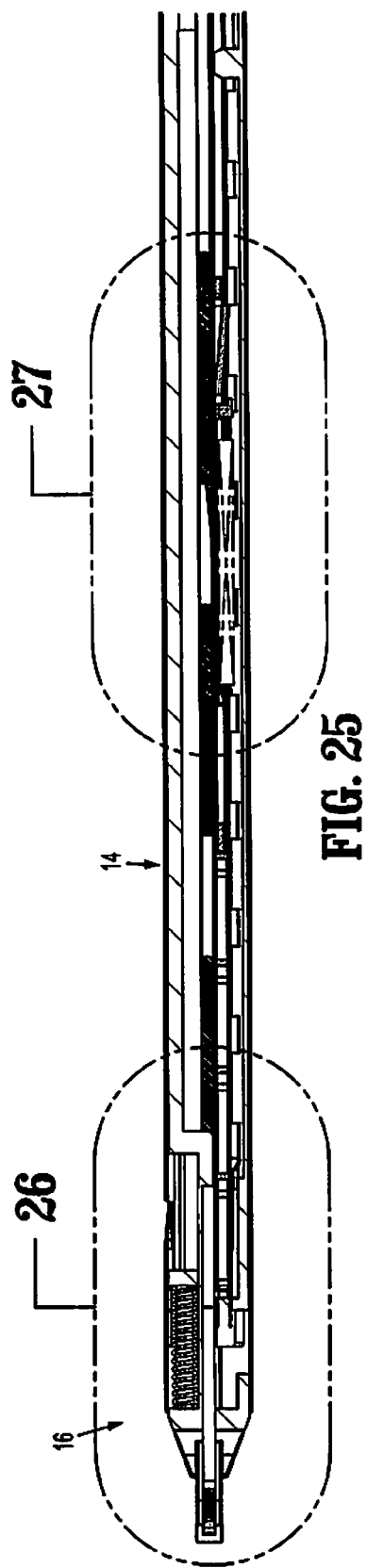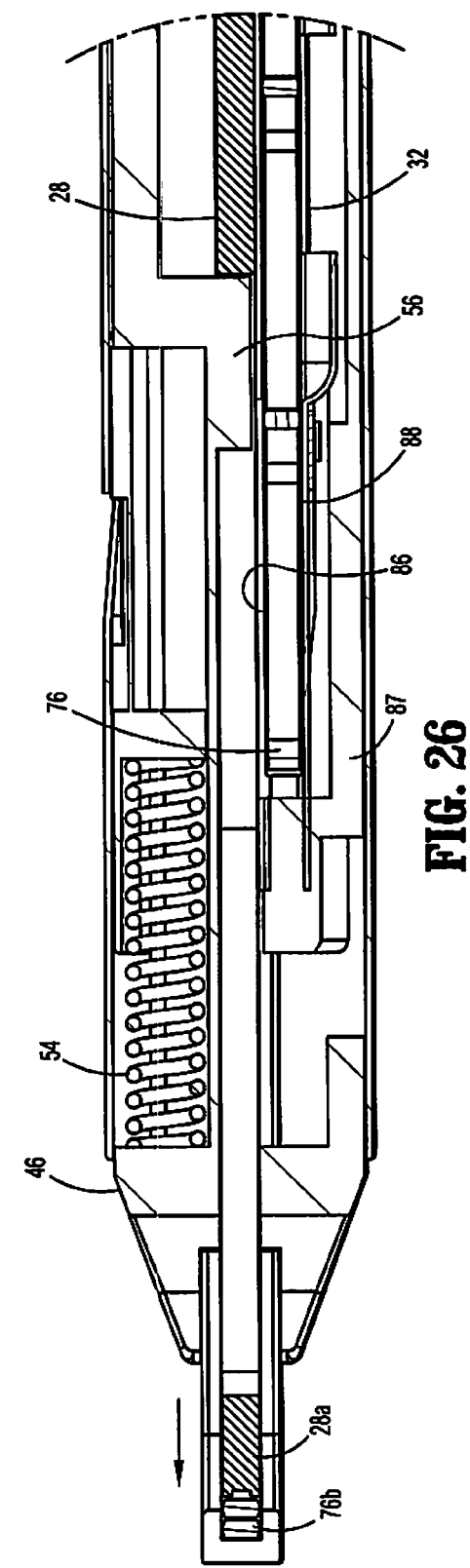

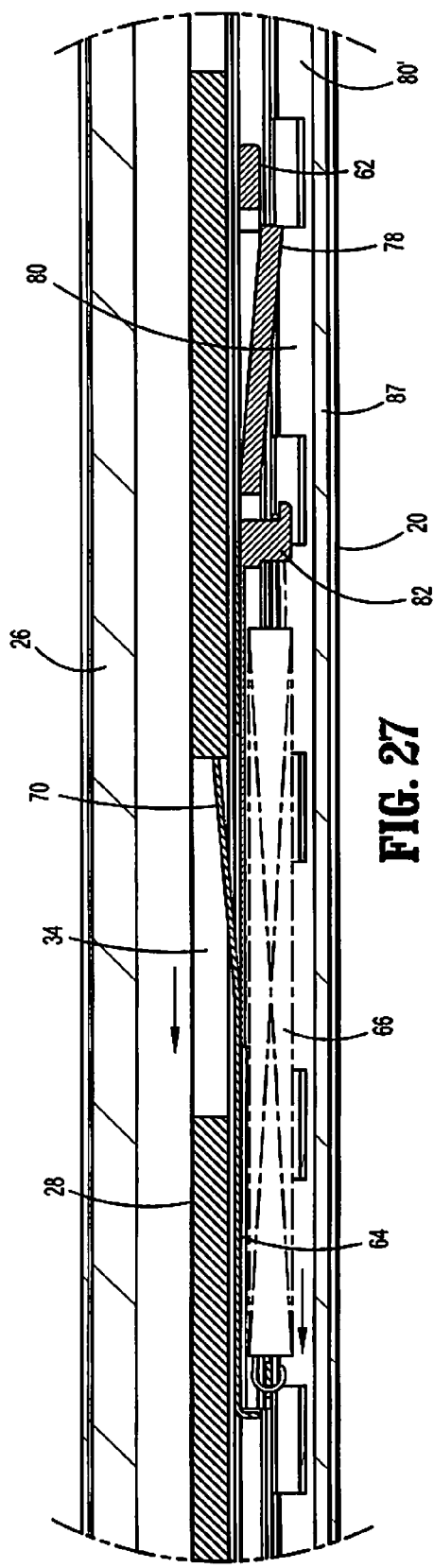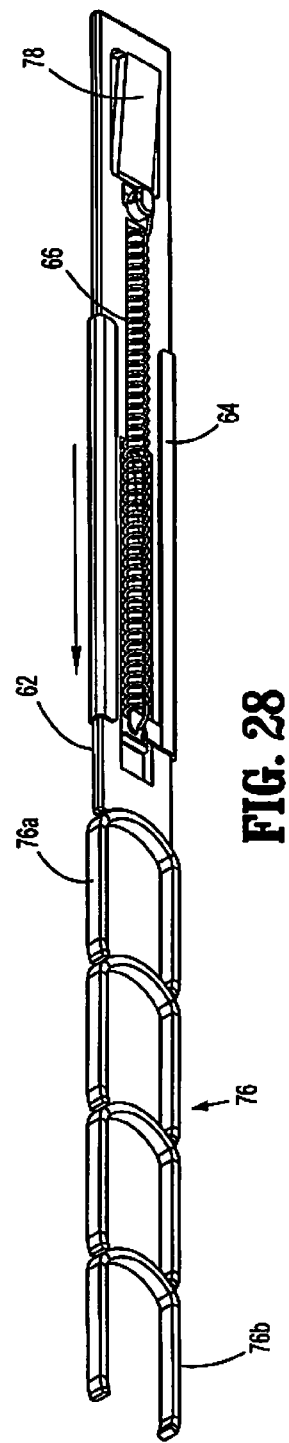

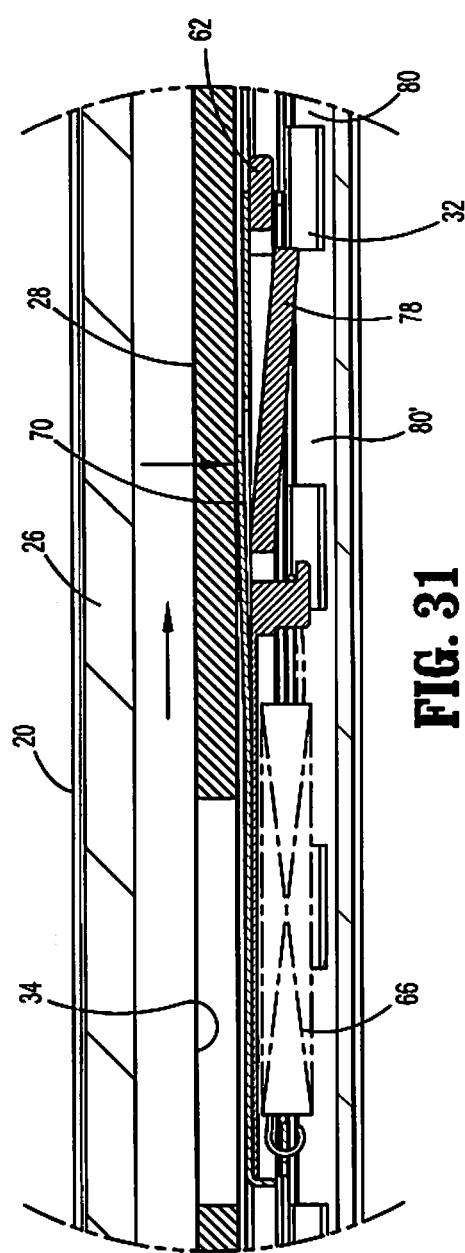
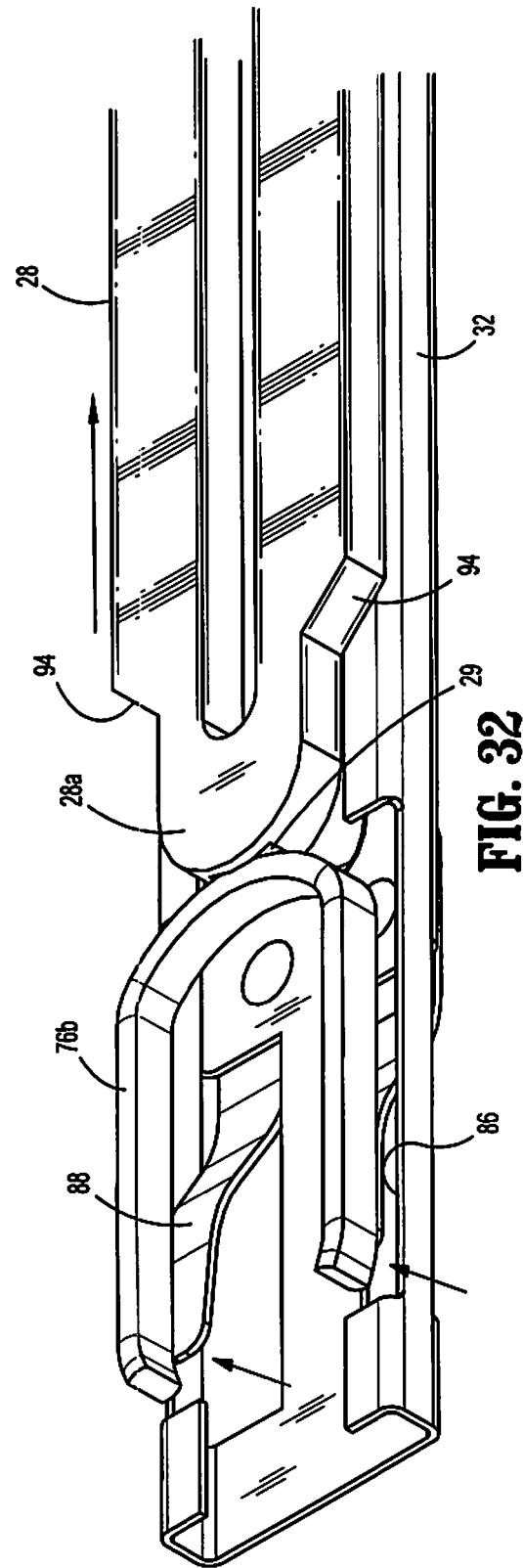

CLIP APPLYING APPARATUS AND LIGATION CLIP

This application claims priority from U.S. Provisional Application Ser. No. 60/612,620, filed Sep. 23, 2004, the contents of which are incorporated herein by reference in its entirety.

BACKGROUND

1. Technical Field

The present disclosure relates to clip applying apparatus and ligation clips. More particularly, the present disclosure relates to a clip applying apparatus for applying surgical clips to body tissue during surgical procedures.

2. Background to Related Art

Surgical procedures frequently require ligation of blood vessels, severed tissues and/or other organs to control or stop bleeding. Clip applying apparatus for quickly applying a surgical clip about tissue are well known. Such clip applying apparatus include single clip applicators and multiple clip applicators. In single clip applicators, a new clip must be loaded into the apparatus after application of each clip. Multiple clip applicators include a series of clips which can be sequentially applied to tissue during the course of a surgical procedure. Because surgical procedures usually require the use of a multiplicity of surgical clips, multiple clip applicators are generally preferred.

Typically, clip applying apparatus include a handle mechanism, an elongated body portion, and a clip crimping assembly, e.g., a jaw or pair of jaws. Such clip applying apparatus are configured for endoscopic or open surgical procedures. One problem associated with known clip applying apparatus is obstructed visualization of the surgical site especially during endoscopic surgical procedures. A continuing need exists for a clip applying apparatus which provides improved visibility of the surgical site during application of a surgical clip to tissue or vessels.

SUMMARY

The presently disclosed clip applying apparatus includes a handle assembly, a central body portion extending distally from the handle assembly, an anvil jaw supported on a distal end of the central body portion and configured to engage a clip, a slide member movably supported in relation to the anvil jaw from a first position to a second position, and a pusher operably associated with the handle assembly. The pusher is movable from a retracted position to an advanced position to deform a clip against the anvil jaw. The anvil jaw and the slide member are configured to define an enclosed tissue receiving area when the slide member is in its second position. In one embodiment, the anvil jaw includes a linear portion and a curved distal portion and the slide member has a distally extending finger which is substantially parallel to the linear portion of the anvil jaw. The distal end of the finger is movable from a position spaced from the curved distal portion of the anvil jaw to a position adjacent the curved distal portion of the anvil jaw to define the enclosed tissue receiving area. The enclosed tissue receiving area can be substantially oval.

In one embodiment, the anvil jaw includes a proximal body portion and the slide member includes a cutout portion. The proximal body portion is slidably positioned within the cutout portion in relation to the anvil jaw.

In another embodiment, the central body portion includes an outer housing and the anvil jaw is fixedly secured to a distal end of the outer housing. A biasing member is positioned to urge the slide member toward its second position. The pusher is operably associated with the slide member such that movement of the pusher to its retracted position effects movement of the slide member to its first position. The pusher can include an elongated slot and the slide member can include a tab positioned within the elongated slot such that a distal wall defining the elongated slot engages the tab during retraction of the pusher to effect movement of the slide member from its first position to its second position.

The clip applying apparatus can also include a clip advancement mechanism and a clip track housing a series of clips. In one embodiment, the clip advancement mechanism has a clip follower positioned to engage the proximal-most clip of the series of clips and the clip advancement mechanism includes a slidable rack and a biasing member positioned between the clip follower and the slidable rack. The slideable rack includes a tab member for releasably engaging the pusher such that when the pusher is moved towards its advanced position, the tab member engages the pusher to move the slidable rack in relation to the clip follower to apply tension to the biasing member and urge the clip follower distally. In this embodiment, when the pusher is in its retracted position, the biasing member of the clip advancement mechanism is not in tension and the clip follower is not urged distally.

In one embodiment, the clip track defines a distally located window dimensioned to allow passage of the distal-most clip and the apparatus includes a retaining spring. The retaining spring is positioned adjacent a distal end of the clip track in a position to urge a distal-most clip of the series of clips from the clip track through the distally located window.

The clip applying apparatus includes at least one clip having a backspan and a pair of spaced legs. In one embodiment, the backspan is curved and each of the spaced legs includes an inwardly curved tip.

In another embodiment, the distal end of the pusher includes a rounded surface positioned to engage the backspan of a distal-most clip of a series of clips to deform the spaced legs along the curved distal portion of the anvil jaw and subsequently collapse the at least one clip into a substantially C-shaped configuration. The distal end of the pusher can include a notch which positioned to engage the backspan of the clip.

The present disclosure also provides a method for applying clip about tissue including the steps of a) providing a clip applying apparatus including at least one clip, an anvil jaw and a slide member movably supported in relation to the anvil jaw between an advanced position and a retracted position, the anvil jaw and the slide member being configured to define an enclosed tissue receiving area when the slide member is in its advanced position; b) positioning the slide member in its retracted position; c) positioning tissue to be ligated adjacent a surface of the anvil jaw; d) moving the slide member to its advanced position to capture tissue within the enclosed tissue receiving area; and e) actuating the clip applying apparatus to deform the at least one clip about the tissue to be ligated.

BRIEF DESCRIPTION OF THE DRAWINGS

Various embodiments of the presently disclosed clip applying apparatus and ligation clip are described herein with reference to the drawings.

FIG. 3C is a perspective view of the central body portion and jaw mechanism of the clip applying apparatus shown in FIG. 1 with the housing removed;

FIG. 3D is an enlarged perspective view of the distal end of the central body portion and jaw mechanism shown in FIG. 3;

FIG. 3E is a top perspective view of the clip advancing mechanism of the clip applying apparatus shown in FIG. 1;

FIG. 3F is a bottom perspective view of the clip advancing mechanism of the clip applying apparatus shown in FIG. 1;

FIG. 3G is a top perspective view of the clip track of the clip applying apparatus shown in FIG. 1;

FIG. 3H is a bottom perspective view of the clip track of the clip applying apparatus shown in FIG. 1;

FIG. 19 is a side cross-sectional view of the central body portion and jaw mechanism of the clip applying apparatus shown in FIG. 1 with the pusher in its retracted position and the slider in its retracted position;

FIG. 20 is an enlarged view of the indicated area of detail shown in FIG. 19;

FIG. 25 is a side cross-sectional view of the central body portion and jaw mechanism of the clip applying apparatus shown in FIG. 1 with the pusher in the fully advanced position and a fully deformed clip positioned in the anvil jaw;

FIG. 26 is an enlarged view of the indicated area of detail shown in FIG. 25;

FIG. 27 is an enlarged view of the indicated area of detail shown in FIG. 25;

FIG. 28 is a perspective view of the clip advancing apparatus and series of clips in the fully advanced position of the pusher;

FIG. 31 is an enlarged view of the indicated area of detail shown in FIG. 29; and FIG. 32 is a top perspective view of the distal end of the clip track and pusher after the pusher has uncovered the clip track window to allow a new clip to be positioned distally of the pusher.

DETAILED DESCRIPTION OF EMBODIMENTS

Figure 1:
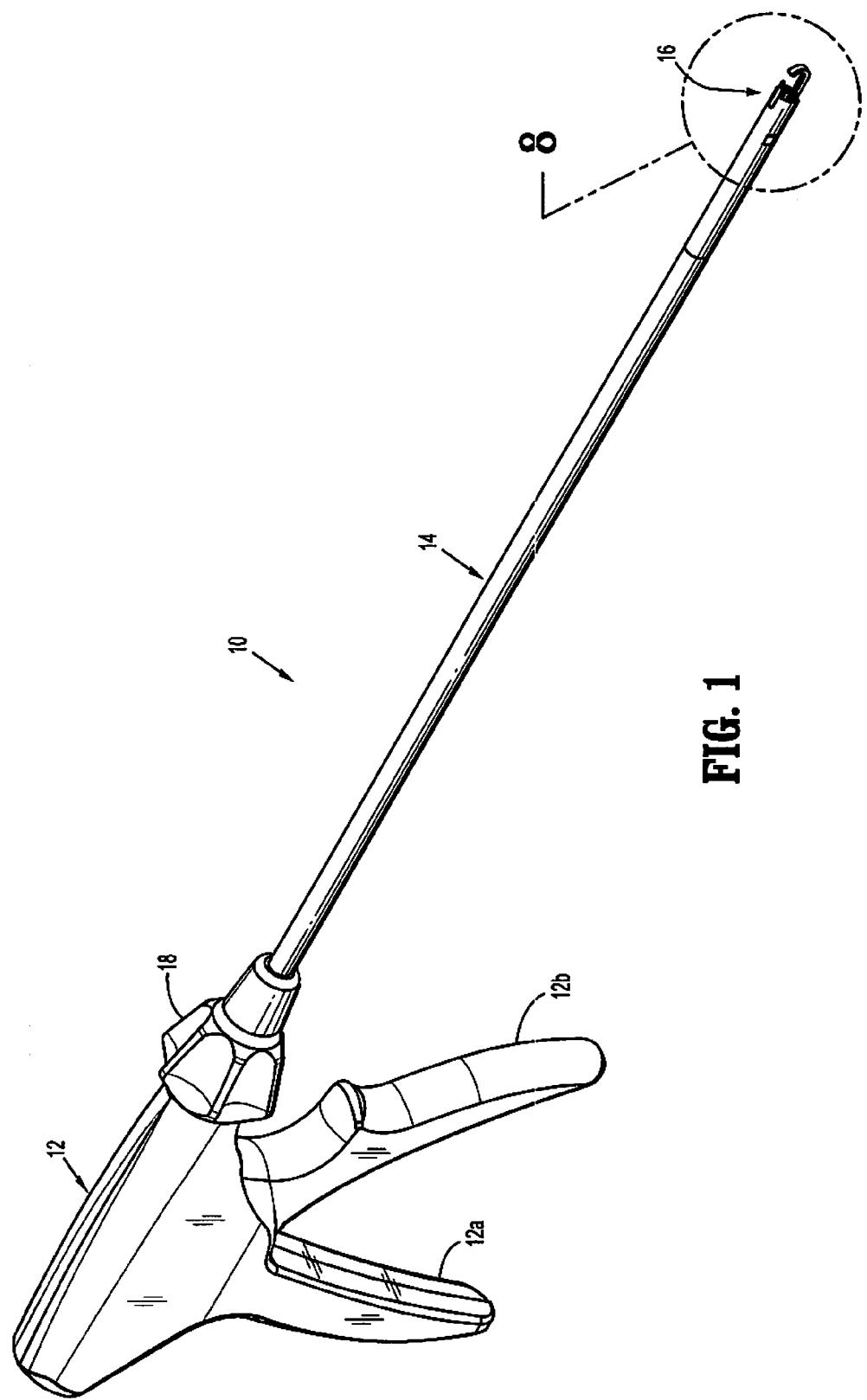
FIG. 1 is a side perspective view of one embodiment of the presently disclosed clip applying apparatus.

Embodiments of the presently disclosed clip applying apparatus and clip will now be described in detail with reference to the drawings, in which like reference numerals designate identical or corresponding elements in each of the several views.

FIG. 1 illustrates one embodiment of the presently disclosed clip applying apparatus 10. Briefly, clip applying apparatus 10 includes a handle assembly 12 including a stationary handle 12a and a pivotable trigger 12b, a central body portion 14 and a jaw mechanism 16. Although handle assembly 12 is illustrated having a pistol grip configuration, other known handle trigger configurations are envisioned, e.g., in-line handle, scissors handle, tweezers handle, multiple triggers, etc. A rotatable knob 18 is rotatably supported on a distal end of handle assembly 12. Rotatable knob 18 supports the proximal end of central body portion 14 in a known manner such that rotatable knob 18, central body portion 14 and jaw mechanism 16 are rotatable in relation to handle assembly 12 about the longitudinal axis of central body portion 14. It is envisioned that rotatable knob 18 may be configured to rotate the jaw mechanism 16 while the central body portion 14 remains stationary. Although specific details of the handle assembly 12 are not disclosed herein, the handle assembly 12 may include any suitable handle mechanism known in the art to effect actuation of a clip pusher mechanism as will be described in detail below. Examples of such known handle mechanisms 12 are disclosed in U.S. Pat. Nos. 5,938,667, 5,868,761, 5,868,759, 5,725,538, 5,720,756, 5,700,270, 5,695,502, 5,645,553, 5,626,585, 5,591,178, 5,514,149, 5,462,558, 5,300,081, 5,197,970 and 4,509,518 which are all incorporated herein in their entirety by reference.

Figure 2:
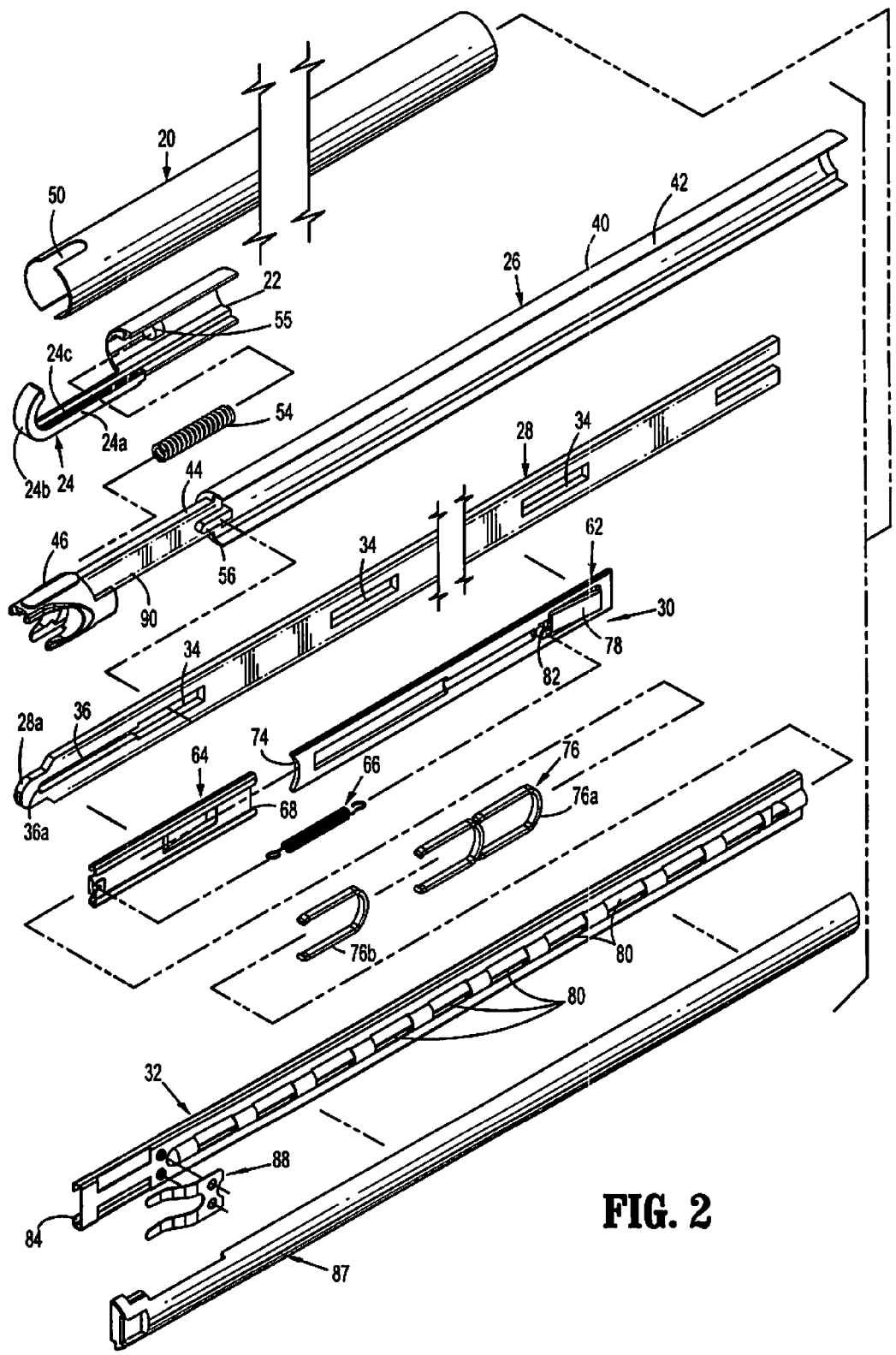
FIG. 2 is an exploded perspective view of the central body portion and jaw mechanism of the clip applying apparatus shown in FIG. 1.
Figure 5:
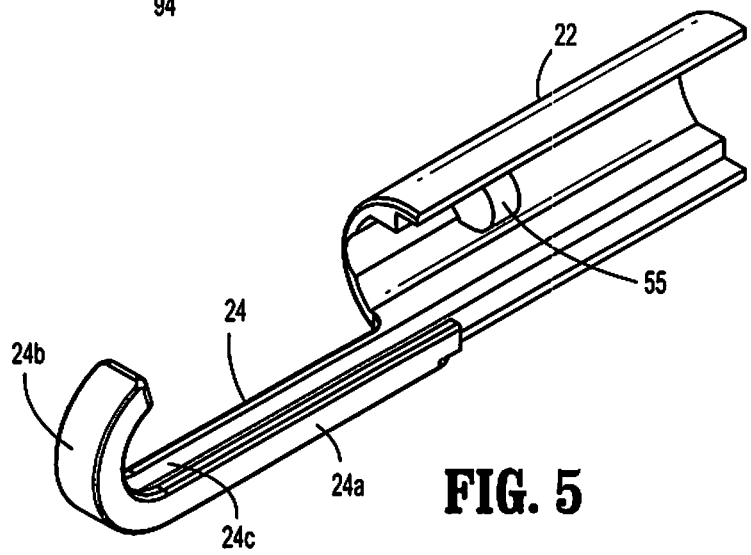
FIG. 5 is an enlarged, side perspective view of the anvil body and jaw of the clip applying apparatus shown in FIG. 1.

Referring to FIGS. 1 and 2, central body portion 14 of clip applying apparatus 10 includes an outer housing 20 which encloses the internal components of central body portion 14. Anvil body 22 is fixedly secured within the distal end of housing 20 using known fastening techniques, e.g., crimping, pins, adhesives, etc. In one embodiment, anvil jaw 24 extends distally from anvil body 22 and includes a linear portion 24a and a semi-circular or curved portion 24b to define a substantially J-shape. Anvil jaw 24 includes a channel 24c for slidably receiving and guiding movement and formation of a clip along anvil jaw 24 as explained in more detail below. (See also FIG. 5 for an enlarged view of the anvil body and jaw).

The internal components of central body portion 14 include an enclosure or slide member 26 which is slidably positioned within housing 20, a pusher 28 for advancing and crimping a distal-most clip 76b from a series of clips, a clip advancement mechanism 30 for distally advancing the series of clips towards anvil jaw 24, and a clip track 32 for guiding and, in association with clip advancement mechanism 30, permitting advancement of the series of clips. More particularly, pusher 28 includes a proximal end operatively connected to handle assembly 12 (not shown) in a known manner. Pusher 28 is slidably positioned within housing 20 such that when pivotable trigger 12b is moved through an actuating stroke, i.e., compressed towards stationary handle 12a, pusher 28 is advanced from a retracted position (See FIG. 19) to an advanced position (See FIG. 25). Pusher 28 includes a plurality of longitudinally spaced channels 34 and a distally-located longitudinal slot 36. Channels 34 and slot 36 are positioned and configured to engage tabs on slide member 26 and on clip advancement mechanism 30, as will be described in further detail below, to control movement of slide member 26 and clip advancement mechanism 30 during movement of pusher 28 from its retracted position to its advanced position.

Figure 3:
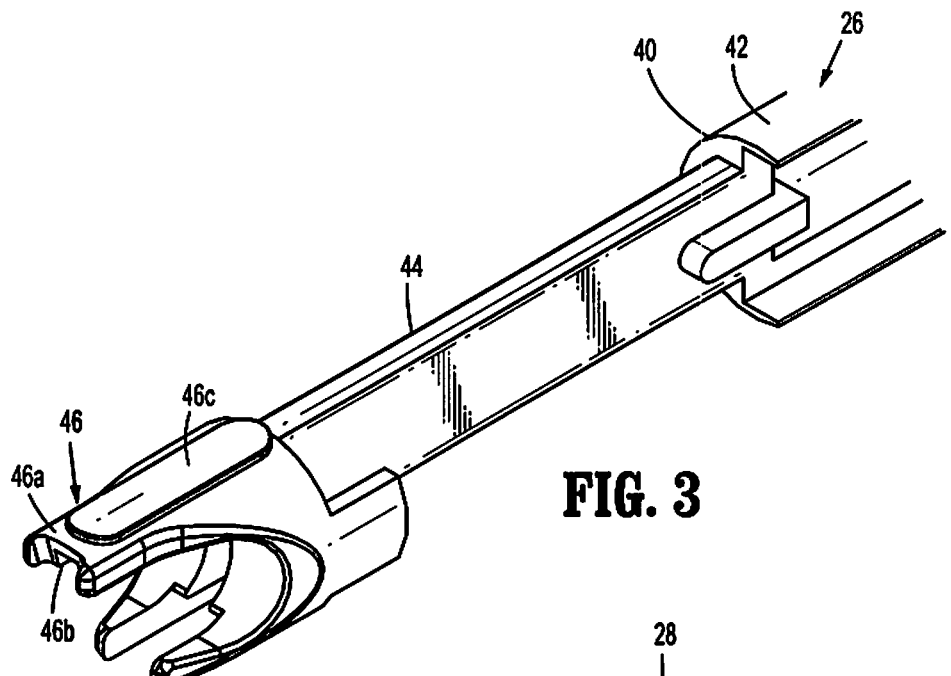
FIG. 3 is an enlarged, side perspective view of the distal end of the slide member of the clip applying apparatus shown in FIG. 1.
Figure 4:
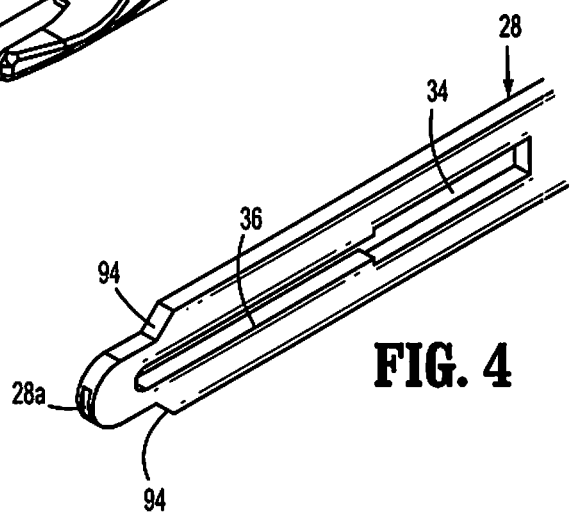
FIG. 4 is an enlarged, side perspective view of the distal end of the pusher of the clip applying apparatus shown in FIG. 1.

Referring also to FIG. 3, slide member 26 includes an elongated body 40 which is slidably positioned within housing 20. Elongated body 40 includes a semi-circular proximal portion 42, a semi-annular cutout portion 44 and a head portion 46 including a distally extending finger 46a. Finger 46a includes a channel 46b for slidably receiving and guiding a clip 76 into anvil jaw 24. Cutout portion 44 is dimensioned to receive anvil body 22 therein. The length of cutout portion 44 is greater than the length of anvil body 22 to permit slide member 26 to slide axially in relation to anvil body 22 between advanced and retracted positions.

Figure 3A:
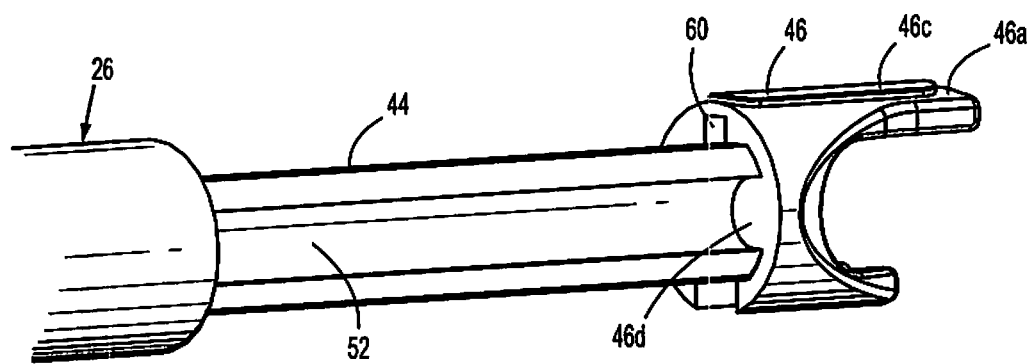
FIG. 3A is an enlarged perspective view from one side of the distal end of the slide member shown in FIG. 3.
Figure 3B:
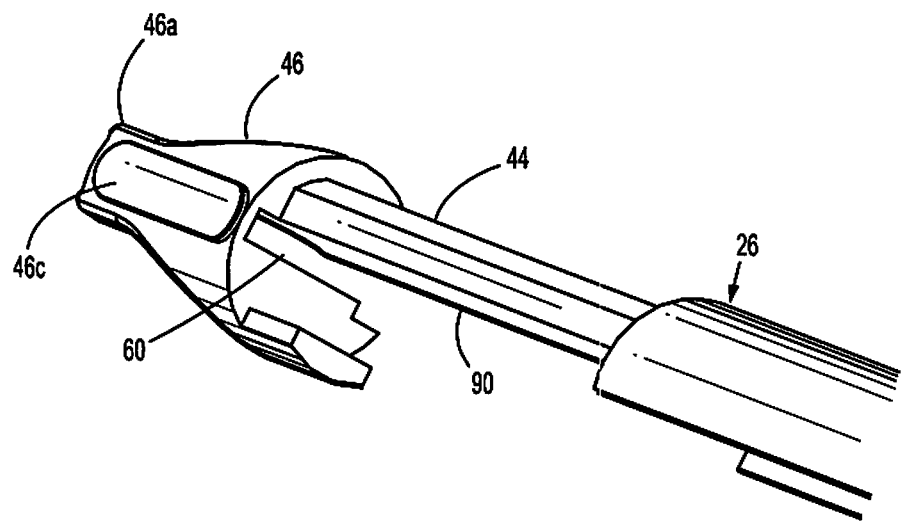
FIG. 3B is an enlarged perspective view from an opposite side of the distal end of the slide member shown in FIG. 3.
Figure 3I:
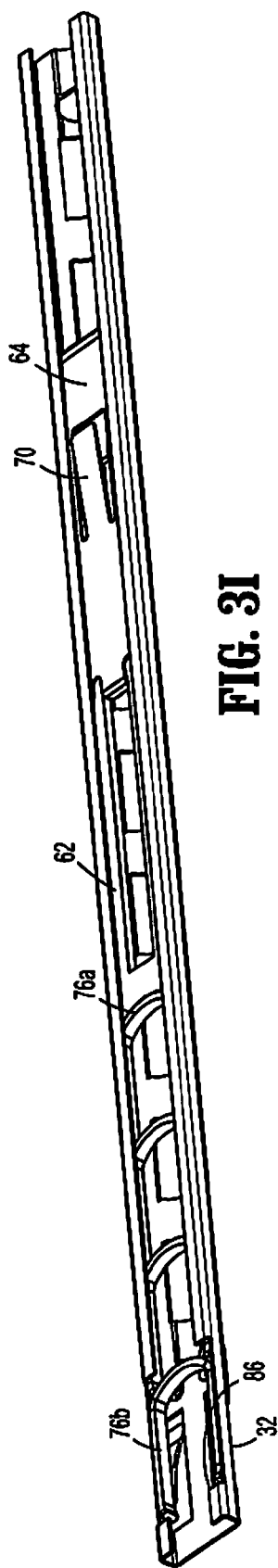
FIG. 3I is a top perspective view of the clip advancing mechanism and clip track assembly of the clip applying apparatus shown in FIG. 3G.

An elongated projection 46c is formed on head portion 46. Projection 46c is slidably received within a slot 50 formed in the distal end of housing 20 to maintain alignment between head portion 46 of slide member 26 and anvil jaw 24 (See FIG. 2). Referring also to FIGS. 3A and 3B, the distal end of slide member 26 has an elongated cavity 52 formed along one side of cutout portion 44 which is dimensioned to receive a biasing member 54, e.g., a coil spring (See FIG. 2). Biasing member 54 is supported in compression within cavity 52 and includes a proximal end engaging an abutment 55 (See FIG. 2) formed on an inner surface of anvil body 22 and a distal end engaging a rear face 46d of head portion 46. Biasing member 54 urges slide member 26 toward its advanced position in which finger 46a engages the distal end of curved portion 24b of anvil jaw 24 to define an enclosed tissue receiving area 25 (See FIG. 3C and FIGS. 8-11). In one embodiment, finger 46a is substantially parallel to linear portion 24a of anvil jaw 24 and tissue receiving area 25 is substantially oval. A tab 56 (See FIG. 2) is formed on slide member 26 and is positioned to be received in slot 36 and distalmost channel 34 of pusher 28. When pusher 28 is being moved to its retracted position, the distal end or wall 36a defining pusher slot 36 engages the forward end of tab 56 to move slide member 26 from its advanced position to its retracted position against the bias of baising member 54. A clip channel or slot 60 (See FIG. 3B) is formed through head portion 46 of slide member 26 to allow passage of the clips 76 into anvil jaw 24. The proximal end of slot 60 is accessible from cutout portion 44.

Central body portion 14 of clip applying apparatus 10 also includes the clip advancement mechanism 30 and a clip track 32. Clip advancement mechanism 30 includes a clip follower 62, a slidable rack 64 and biasing member 66, e.g., a coil spring. Referring also to FIGS. 3E and 3F, slidable rack 64 defines a C-shaped channel 68 dimensioned to slidably receive clip follower 62 and includes a resilient tab 70 which is dimensioned and configured to be received within channels 34 of pusher 28. A finger 64a formed on slidable rack 64 extends into an elongated slot 62a formed in clip follower 62 to maintain rack 64 and follower 62 in alignment. A spring engagement member 72 is formed at the distal end of slidable rack 64. A distal end of biasing member 66 is secured to engagement member 72 of slidable rack 64.

Clip follower 62 includes a concave or curved distal end 74 configured to engage a backspan of the proximal-most clip 76a of a series of clips 76. A resilient tab 78 is formed at the proximal end of clip follower 62. Tab 78 is configured to be received within recesses or openings 80 formed in clip track 32 to prevent proximal movement of follower 62 in relation to clip track 32 (See FIG. 3S). Because of the angle of tab 78, distal movement of follower 62 in relation to clip track 32 is permitted. A spring engagement member 82 is formed on clip follower 62. The proximal end of biasing member 66 is secured to engagement member 82. Biasing member 66 is supported in tension between slidable rack 64 and clip follower 62 to facilitate incremental advancement of the series of clips 76 in a manner to be described in further detail below.

Figure 3J:
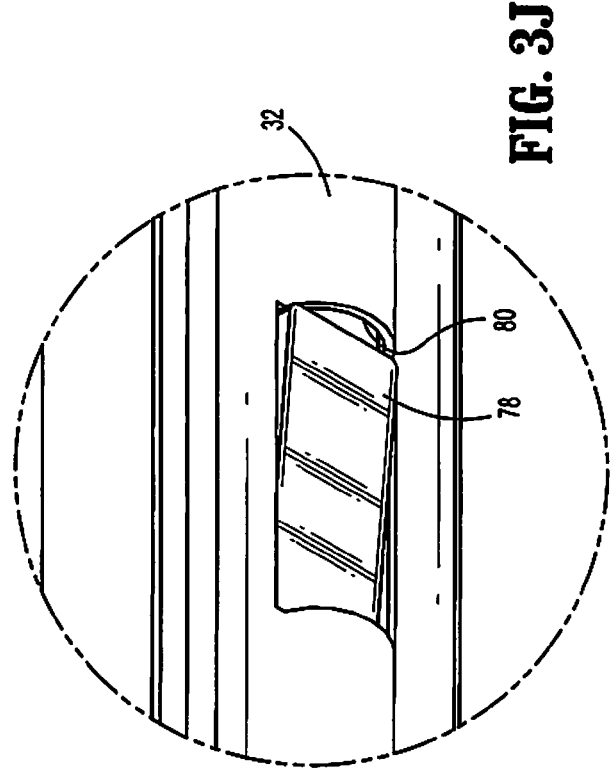
FIG. 3J is an enlarged view of the indicated area of detail shown in FIG. 3C.
Figure 18:
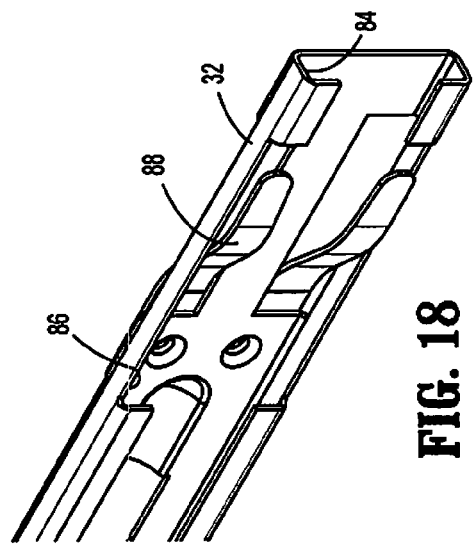
FIG. 18 is a perspective cutaway view of the distal end of the clip advancing mechanism of the clip applying apparatus shown in FIG. 1.

Referring to FIG. 2 and FIGS. 3G-3I, clip track 32 also defines a C-shaped channel 84 dimensioned to slidably receive the series of clips 76 and clip advancement mechanism 30. The series of clips 76 is positioned in the distal end of C-shaped channel 84 and the clip advancement mechanism 30 is positioned in the proximal end of C-shaped channel 84 with clip follower 62 engaging the proximal-most clip 76a of the series of clips 76. As discussed above, clip track 32 includes a series of longitudinally spaced openings 80. Each opening 80 is dimensioned to receive resilient tab 78 of clip follower 62 to prevent proximal movement of clip follower 62 in relation to clip track 32 (FIG. 3J). The distal end of C-shaped channel 84 includes a window or opening 86 (FIG. 3G) which allows a clip to exit C-shaped channel 84 to a position distally of the distal end of pusher 28. A retaining spring 88 (FIG. 2) is secured to the distal end of clip track 32 adjacent window 86 to urge the distal-most clip 76b from C-shaped channel 84 against a sidewall 90 (FIG. 3B) within cutout 44 of slide member 26 adjacent clip slot 60. Retaining spring 88 also functions to secure the distal-most clip 76b against sidewall 90 of cutout 44 adjacent clip slot 60 until pusher 28 is actuated via pivotable trigger 12b to apply the clip 76b to tissue. (See FIG. 18).

Referring again to FIG. 2, a clip track cover 87 is secured to a top surface of clip track 32. Cover 87 may be formed from a clear material to permit visualization of the clips remaining in the apparatus.

Figure 6:
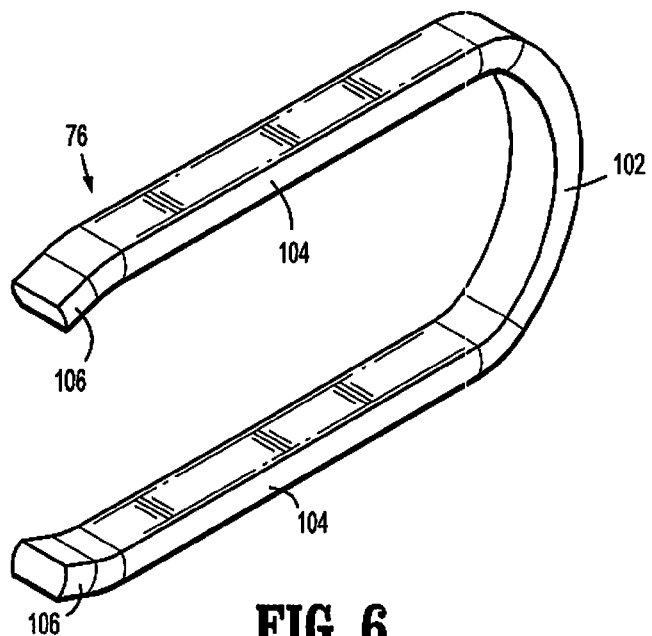
FIG. 6 is a side perspective view of a surgical clip for use with the clip applying apparatus shown in FIG. 1.
Figure 7:
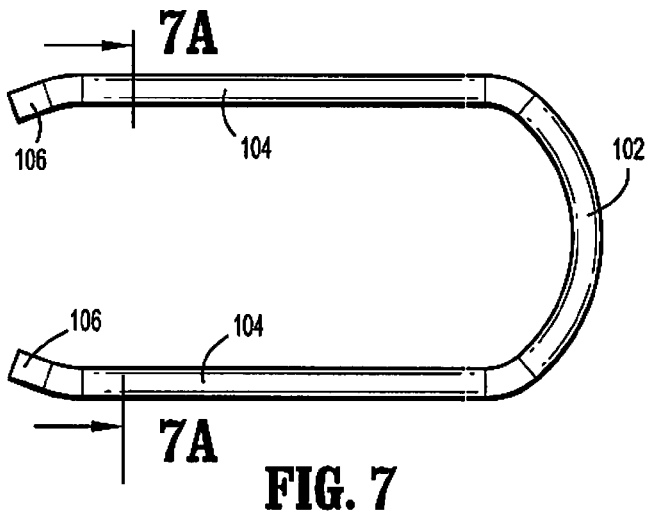
FIG. 7 is a top view of the surgical clip shown in FIG. 6.
Figure 7A:
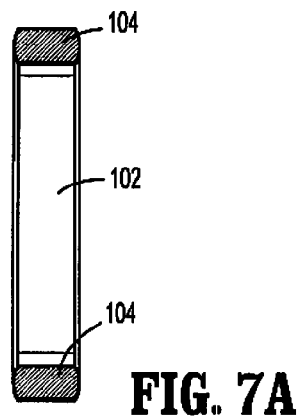
FIG. 7A is a cross-sectional view taken along section lines 7A-7A of FIG. 7.
Figure 8:
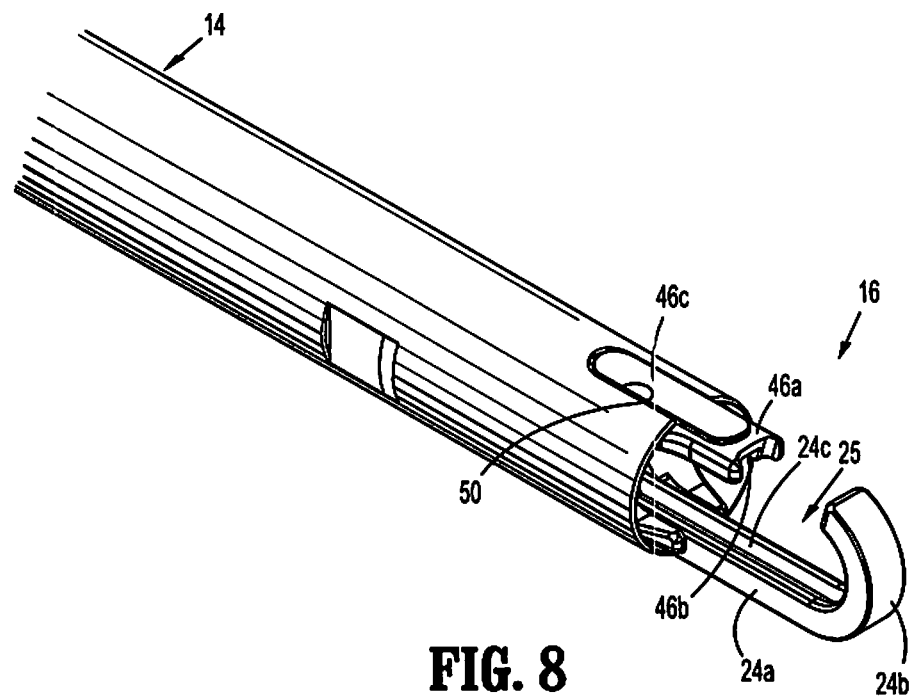
FIG. 8 is a side perspective cutaway view of the distal end of the clip applying apparatus shown in FIG. 1 with the jaw in the open position.
Figure 9:
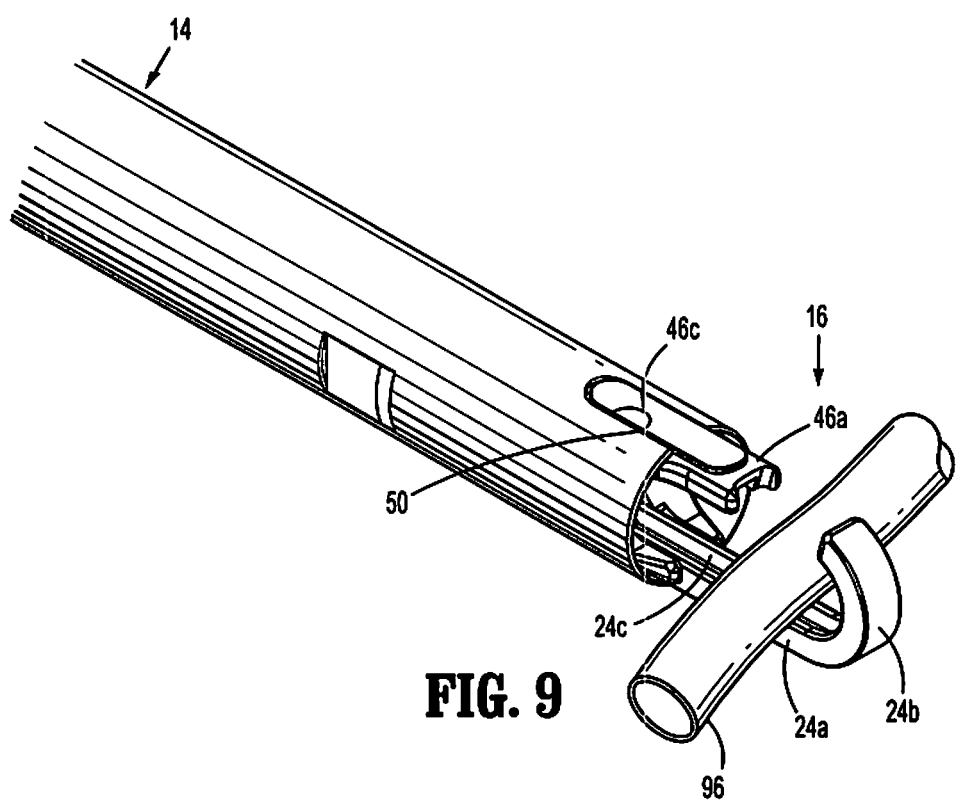
FIG. 9 is a side perspective cutaway view of the distal end of the clip applying apparatus shown in FIG. 8 with a vessel positioned in the open anvil jaw.

FIGS. 6 and 7 illustrate one embodiment of a ligating clip shown generally as 76. Ligating clip 76 includes a backspan 102 and a pair of legs 104. Backspan 102 may be curved or semi-circular. Alternately, other configurations are envisioned. Each leg 104 is substantially parallel to the other leg and may include a curved tip 106 which curves generally towards the other of the clip legs. Curved tips 106 allow the legs to smoothly traverse curved channel 24c of anvil jaw 24 without binding within the jaw during deformation of the clip 76. In a particularly useful embodiment, clip 76 is constructed from a surgical grade metal such as titanium. Alternately, other materials suitable for surgical use and having the requisite strength and deformation characteristics may be used to construct the clip 76.

Figure 16:
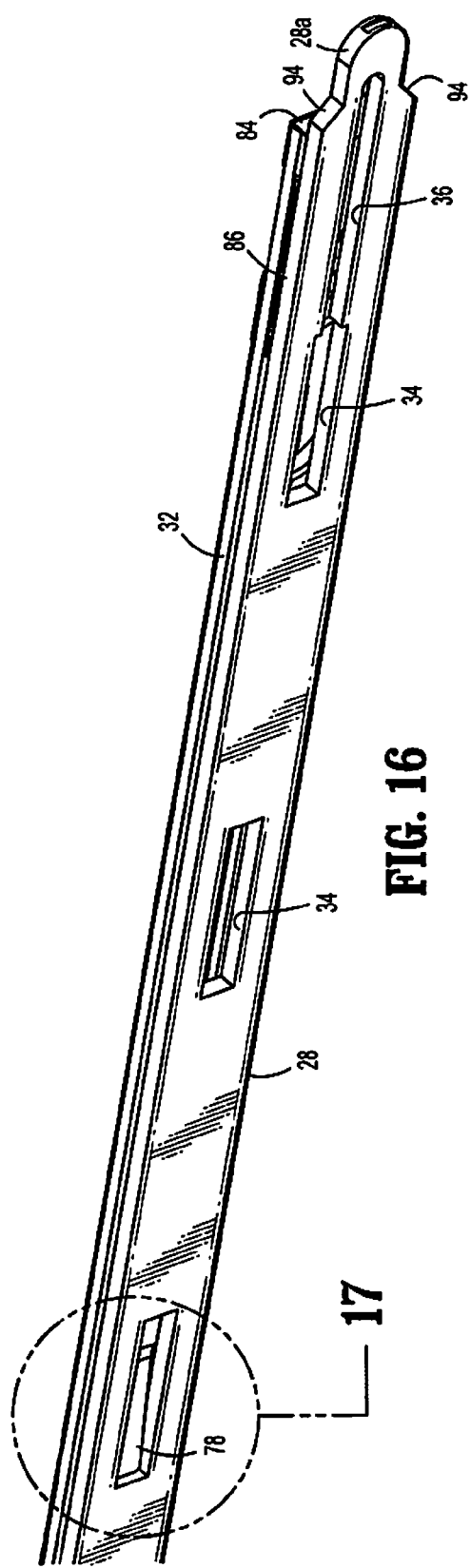
FIG. 16 is a perspective cutaway view of the pusher, slide track and clip advancing mechanism in an assembled condition with the pusher partially advanced.
Figure 17:
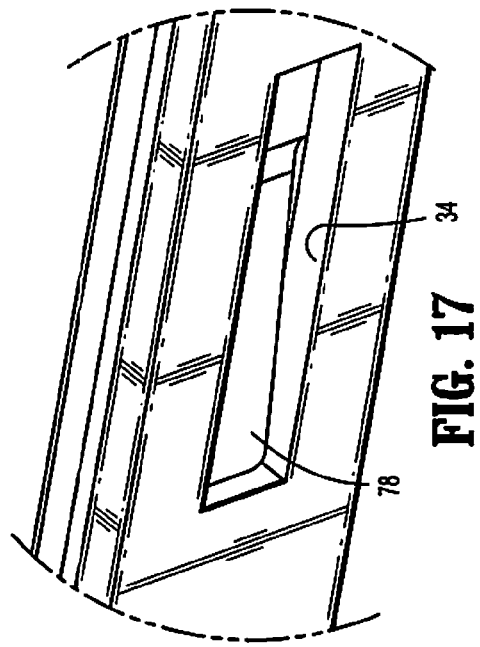
FIG. 17 is an enlarged view of the indicated area of detail of FIG. 16.
Figure 21:
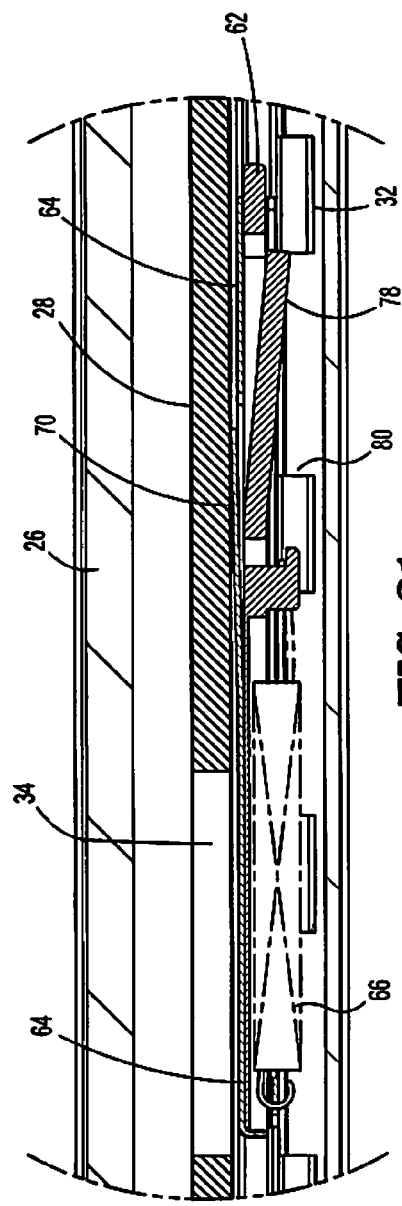
FIG. 21 is an enlarged view of the indicated area of detail shown in FIG. 19.

Referring to FIGS. 2 and 19-21, prior to actuation of clip applying apparatus 10, pusher 28 is maintained in its retracted position in a known manner by handle assembly 12. In the retracted position, pusher 28 retains slide member 26 in its retracted position. More specifically, when pusher 28 is moved to the retracted position, the distal end 36a of slot 36 formed in pusher 28 engages tab 56 of slide member 26 to move slide member 26 to its retracted position with pusher 28 against the bias of biasing member 54 which is in compression (See FIG. 20). Resilient tab 78 of clip follower 62 is engaged within an opening 80 (See FIGS. 16, 17 and 21) of clip track 32 to retain clip follower 62 at a position in which the distal end 74 of clip follower 62 is engaged with the proximal-most clip 76a (See FIG. 2B). Biasing member 66 is not in tension (or compression). Thus, no substantial axial force is being applied to the series of clips 76 by clip follower 62. Slidable rack 64 is supported about clip follower 62. The distal-most clip 76b is positioned against sidewall 90 within cutout portion 44 of slider 46 adjacent clip slot 60 at a position distally of the distal end of pusher 28.

Figure 22:
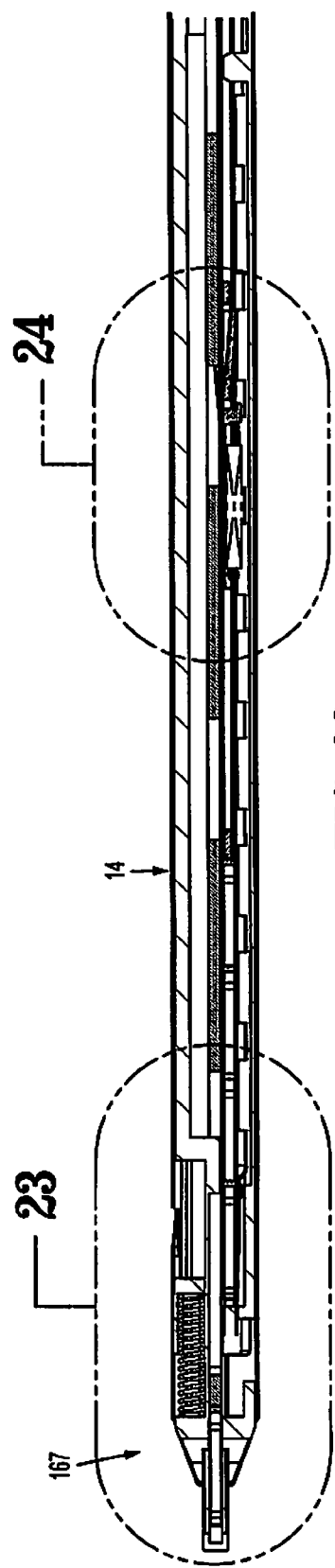
FIG. 22 is a side cross-sectional view of the central body portion and jaw mechanism of the clip applying apparatus shown in FIG. 1 with the pusher partially advanced to position a clip in the anvil jaw, the slide rack partially advanced and the slide member fully advanced to close the jaw mechanism.
Figure 23:
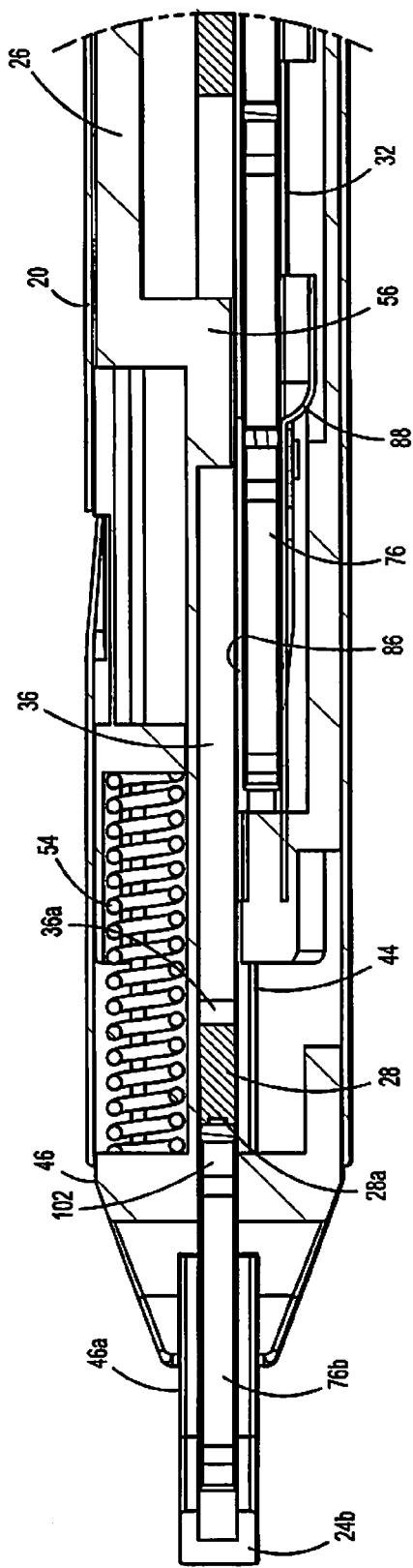
FIG. 23 is an enlarged view of the indicated area of detail shown in FIG. 22.
Figure 24:
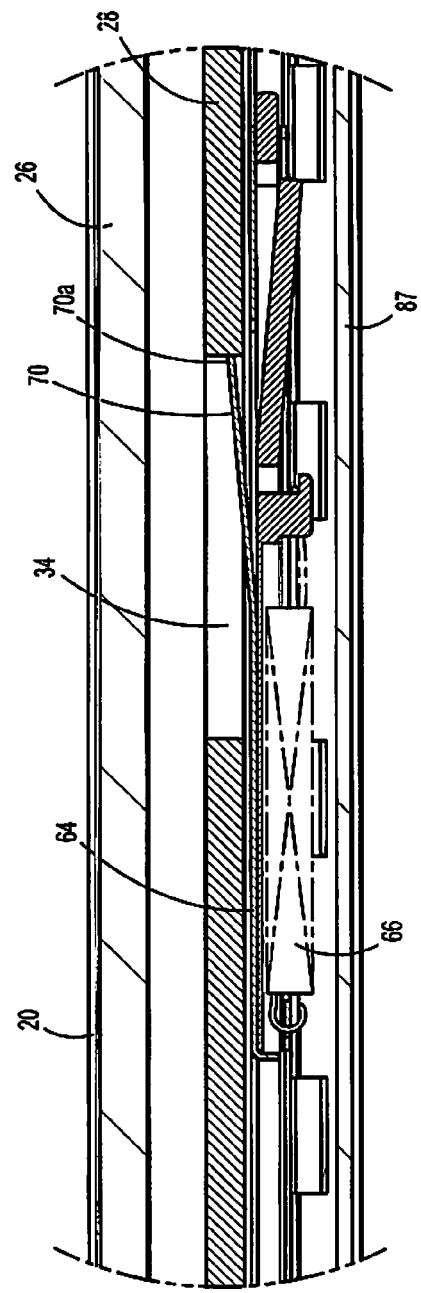
FIG. 24 is an enlarged view of the indicated area of detail shown in FIG. 22.
Figure 29:
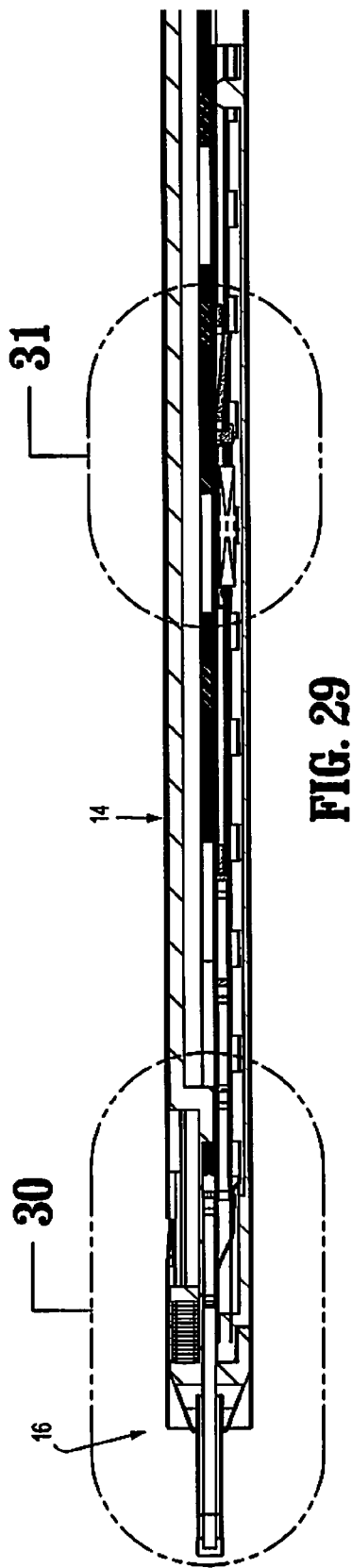
FIG. 29 is a side cross-sectional view of the central body portion and jaw mechanism of the clip applying apparatus shown in FIG. 1 with the pusher partially retracted, the slide member fully retracted and a new clip positioned distally of the distal end of the pusher.

Referring to FIGS. 22-24, when pivotable trigger 12b (See FIG. 1) is actuated to distally advance pusher 28 within housing 20, slot 36 of pusher 28 is moved distally in relation to tab 56 of slide member 26 (See FIG. 23). Since the distal end 36a of slot 36 no longer retains slide member 26 in its proximal position, biasing member 54 urges slide member 26 distally with pusher 28 to its advanced position. In its advanced position, head portion 46 of slide member 26 is positioned such that finger 46a abuts the distal end of curved portion 24b to define enclosed tissue receiving area 25 (See FIG. 10).

During distal advancement of pusher 28, resilient tab 70 of slidable rack 64 is received within channel 34 of pusher 28 (See FIG. 24). When the proximal edge 70a of tab 70 engages the proximal end of channel 34, slidable rack 64 is advanced distally with pusher 28. As slidable rack 64 moves distally, biasing member 66 is put in tension to urge clip follower 62 distally. However, because pusher 28 is positioned over window 86 (See FIG. 23) of clip track 32, the series of clips 76 and thus clip follower 62, cannot advance distally. As a result, slidable rack 64 is advanced distally with pusher 28 over clip follower 62 increasing the length and the tension in biasing member 66.

Figure 10:
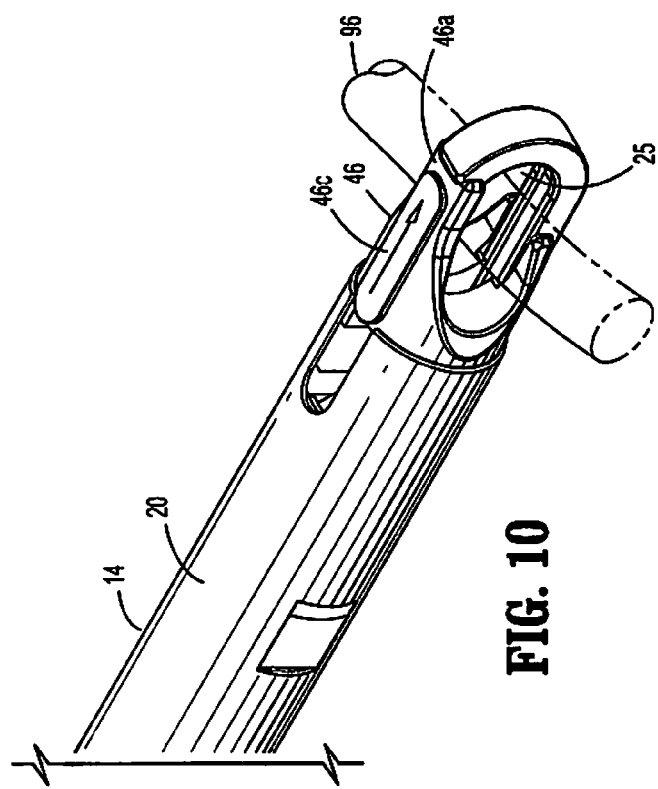
FIG. 10 is a side perspective cutaway view of the distal end of the clip applying apparatus shown in FIG. 9 with the anvil jaw in the closed position and a vessel positioned within a clip.
Figure 11:
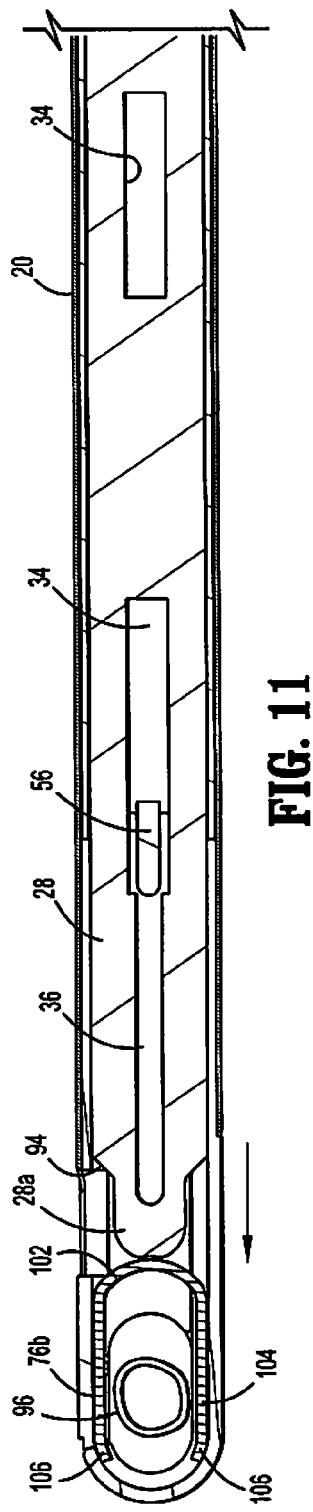
FIG. 11 is a side cross-sectional cutaway view of the distal end of the clip applying apparatus shown in FIG. 1 in the closed position with a vessel positioned within a clip.

At a point during advancement of pusher 28, the distal end 28a of pusher 28 engages the backspan 102 of distal-most clip 76b and advances distal-most clip 76b through clip slot 60 along anvil jaw channel 24c and channel 46b of finger 46a of head portion 46 into anvil jaw 24 (See also FIGS. 10 and 11).

When pusher 28 passes distally over window 86 of clip track 32, pusher 28 covers window 86 to prevent the second distal-most clip from being pushed through window 86 by retaining spring 88. As such, series of clips 76 still cannot move distally, and clip follower 62 remains in its original position prior to actuation of clip applying apparatus 10.

Figure 12:
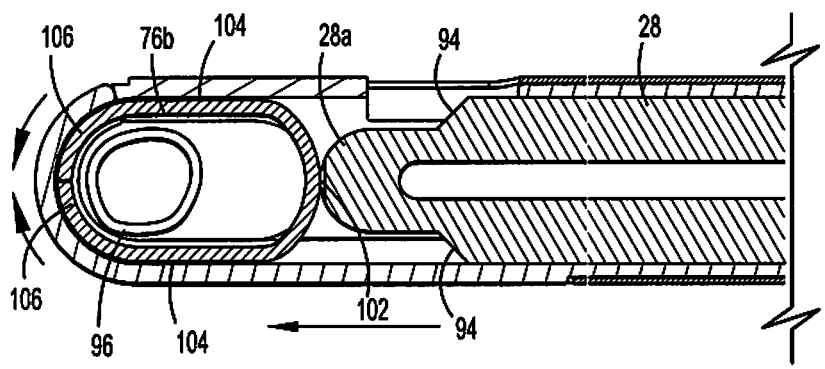
FIG. 12 is a side cross-sectional cutaway view of the distal end of the clip applying apparatus shown in FIG. 1 with a vessel positioned within a clip in the anvil jaw and the pusher advanced to partially deform the clip.
Figure 13:
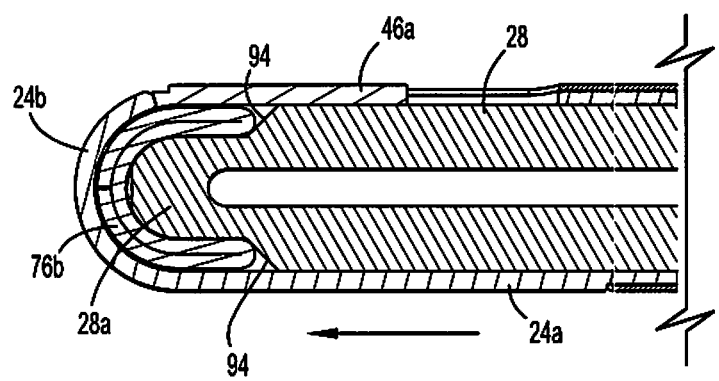
FIG. 13 is a side cross-sectional cutaway view of the distal end of the clip applying apparatus shown in FIG. 1 with a vessel positioned within a clip in the anvil jaw and the pusher advanced to fully deform the clip.
Figure 14:
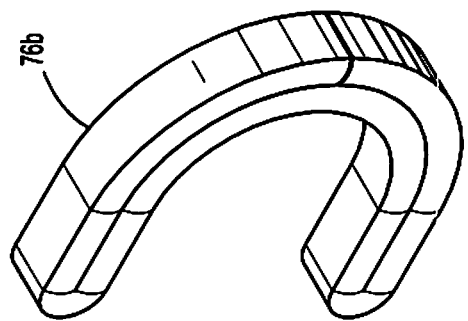
FIG. 14 is a side perspective view of the clip shown in FIG. 6 after the clip has been fully deformed as shown in FIG. 13.

Referring to FIGS. 25-27, when clip 76b is positioned within anvil jaw 24, continued advancement of pusher 28 first deforms the clip into a substantially oval configuration about tissue 96 (See FIG. 12) and thereafter, collapses one end of the clip into the inside surface of the other end of the clip to form an overlapping C-shaped deformed clip about tissue 96 (See FIGS. 13 & 14). The distal end 28a of pusher 28 includes a rounded surface or nose of reduced width to effect collapse of the oval partially deformed clip 76b onto itself. A pair of tapered diverging shoulders 94 (FIG. 32) extend between distal end 28a of pusher 28 and an outer sidewall of pusher 28. Diverging shoulders 94 urge the clip into a substantially closed C-shaped configuration during the final stage of clip formation.

Figure 15:
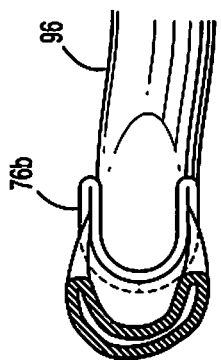
FIG. 15 is a perspective partial cross-sectional view illustrating a fully deformed clip positioned about a vessel.

After clip 76b is fully deformed about a vessel (See FIG. 15), pivotable trigger 12b (See FIG. 1) is released and pusher 28 is returned from its advanced position to its retracted position in a known manner, e.g., a retraction spring located in the handle assembly or central body portion (not shown). Referring to FIGS. 28-31, as pusher 28 moves to its retracted position, biasing member 66, which is in tension begins to return slidable rack 64 to its retracted position. When distal end of pusher 28 is retracted such that it passes over and uncovers window 86 of clip track 32, biasing member 66, which is still in tension, urges clip follower 62 distally (See FIG. 28). As such, when pusher 28 uncovers window 86, retaining spring 88 pushes the next clip of the series of clips 76 through window 86 against sidewall 90 of slide member 26 adjacent clip slot 60. After the next clip of the series of clips 76 is moved through window 86, biasing member 66 urges clip follower 62 distally to advance the series of clips 76 distally to position the second clip of series of clips 76 to a position beneath window 86 (See FIGS. 30 and 32). As clip follower 62 advances distally, resilient tab 78 (FIG. 27) of clip follower 62 disengages with the opening 80 of clip track 32 with which it was engaged and reengages with the next distally positioned opening 80' (FIG. 31) in clip track 32. As pusher 28 continues to move to its retracted position to allow slidable rack 64 to move proximally, the tension in biasing member 66 is relieved and substantially all axial forces on the series of clips 76 by the clip follower 62 are removed.

Figure 30:
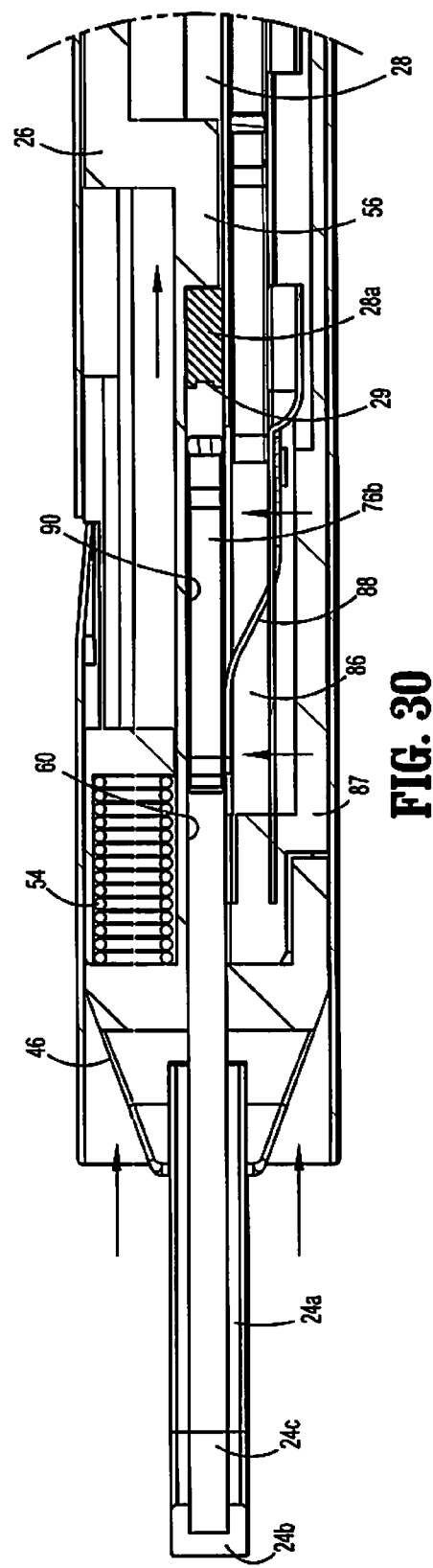
FIG. 30 is an enlarged view of the indicated area of detail shown in FIG. 29.

As pusher 28 continues to move to its proximal-most position, the distal end 36a of slot 36 in pusher 28 engages tab 56 of slide member 26 and moves slide member 26 from its advanced position to its retracted position against the bias of biasing member 54 (FIG. 30). Movement of slide member 26 from its advanced position to its retracted position moves finger 46a of head portion 46 of slide member 26 proximally away from curved portion 24b of anvil jaw 24 to open jaw mechanism 16 and provide access to receiving area 25.

As best illustrated in FIGS. 30 and 32, the distal end 28a of pusher 28 may include a notch 29 which is dimensioned to partially engage the backspan 102 of clip 76. It is envisioned that notch 29 provides additional support and guides the clip 76 during the entire deformation of clip 76.

Clip applying apparatus 10 may be constructed from any suitable medical grade material including plastics and metals suitable for use in medical instrumentation. For example, the anvil body and/or jaw and other high force bearing components of the clip applying apparatus 10 may be constructed from surgical grade metals, whereas the clip follower 62 and other minimal force bearing components of the clip applying apparatus 10 may be formed from surgically approved plastics.

The benefits of the presently disclosed clip applying apparatus include improved visibility at the surgical site. Visibility is improved because the curved anvil jaw 24 is less obstructed by the distal components of the apparatus. Further, the curved or hooked anvil jaw 24 simplifies positioning of tissue within the anvil jaw 24. Moreover, the slide member (i.e., finger 46a) encloses the tissue receiving area 25 of anvil jaw 24 and prevents separation of anvil jaw 24 and tissue during manipulation and actuation of the apparatus.

Although the illustrative embodiments of the present disclosure have been described herein with reference to the accompanying drawings, it is to be understood that this disclosure is not limited to those precise embodiments and that various other changes and modifications may be affected therein by one skilled in the art without departing from the scope or spirit of the disclosure. All such changes and modifications are intended to be included within the scope of any appended claims.

What is claimed is:

1. A clip applying apparatus comprising:
   a handle assembly;
   a central body portion extending distally from the handle assembly;
   an anvil jaw supported on a distal end of the central body portion, the anvil jaw being configured to engage a clip;
   a slide member movably supported in relation to the anvil jaw for distal movement from a first position to a second position;
   a pusher operably associated with the handle assembly, the pusher being distally movable from a retracted position to an advanced position to engage and deform a clip against the anvil jaw, wherein the slide member and the pusher are configured and dimensioned such that the slide member and the pusher are distally movable independently of each other; and
   a clip advancement mechanism and a clip track housing a series of clips, the clip advancement mechanism including a clip follower positioned to engage a proximal-most clip of the series of clips to advance the series of clips, wherein the anvil jaw and the slide member are configured to define an enclosed tissue receiving area when the slide member is in its second position and the pusher is spaced from the advanced position.

2. A clip applying apparatus according to claim 1, wherein the anvil jaw includes a linear portion and a curved distal portion and the slide member has a distally extending finger which is substantially parallel to the linear portion of the anvil jaw, the distal end of the finger being movable from a position spaced from the curved distal portion of the anvil jaw to a position adjacent the curved distal portion of the anvil jaw to define the enclosed tissue receiving area.

3. A clip applying apparatus according to claim 2, further including at least one clip, the at least one clip having a backspan and a pair of spaced legs.

4. A clip applying apparatus according to claim 3, wherein the backspan is curved and each of the spaced legs includes an inwardly curved tip.

5. A clip applying apparatus according to claim 4, wherein the distal end of the pusher includes a rounded surface positioned to engage the backspan of the at least one clip and deform the spaced legs along the curved distal portion of the anvil jaw and subsequently collapse the at least one clip into a substantially C-shaped configuration.

6. A clip applying apparatus according to claim 5, wherein the distal end of the pusher includes a notch which positioned to engage the backspan of the at least one clip.

7. A clip applying apparatus according to claim 1, wherein the enclosed tissue receiving area is substantially oval.

8. A clip applying apparatus according to claim 1, wherein the anvil jaw includes a proximal body portion and the slide member includes a cutout portion, the proximal body portion being slidably positioned within the cutout portion.

9. A clip applying apparatus according to claim 1, wherein the central body portion includes an outer housing, the anvil jaw being fixedly secured to a distal end of the outer housing.

10. A clip applying apparatus according to claim 9, further including a biasing member positioned to urge the slide member toward its second position.

11. A clip applying apparatus according to claim 10, wherein the pusher is operably associated with the slide member such that movement of the pusher to its retracted position effects movement of the slide member to its first position.

12. A clip applying apparatus according to claim 11, wherein the pusher includes an elongated slot and the slide member includes a tab positioned within the elongated slot, a distal wall defining the elongated slot engaging the tab during retraction of the pusher to effect movement of the slide member from its first position to its second position.

13. A clip applying apparatus according to claim 1, wherein the clip advancement mechanism further includes a slidable rack and a biasing member positioned between the clip follower and the slidable rack.

14. A clip applying apparatus according to claim 13, wherein the slidable rack includes a tab member for releasably engaging the pusher such that when the pusher is moved towards its advanced position, the tab member engages the pusher to move the slidable rack in relation to the clip follower to apply tension to the biasing member and urge the clip follower distally.

15. A clip applying apparatus according to claim 14, wherein when the pusher is in its retracted position, the biasing member of the clip advancement mechanism is not in tension and the clip follower is not urged distally.

16. A clip applying apparatus according to claim 1, wherein the clip track defines a distally located window dimensioned to allow passage of the distal-most clip.

17. A clip applying apparatus according to claim 16, further including a retaining spring positioned adjacent a distal end of the clip track, the retaining spring being positioned to urge a distal-most clip of the series of clips from the clip track through the distally located window.

18. A clip applying apparatus according to claim 1, wherein the slide member and the pusher are configured and dimensioned such that the slide member is moved into the second position prior to movement of the pusher into the advanced position, whereby the clip is moved into the enclosed tissue receiving area prior to deformation.

19. A clip applying apparatus according to claim 1, wherein the pusher is configured and dimensioned to engage a clip in the series of clips to thereby deform the clip against the anvil jaw.

20. A clip applying apparatus comprising:
   a handle assembly;
   a central body portion including a proximal end and a distal end, the central body portion extending distally from the handle assembly;
   an anvil jaw supported on the distal end of the central body portion, the anvil jaw being configured to engage a clip;

a slide member movably supported in relation to the anvil jaw for distal movement from a first position to a second position;

a pusher operably associated with the handle assembly, the pusher being distally movable from a retracted position to an advanced position to engage and deform a clip against the anvil jaw. wherein the slide member and the pusher are configured and dimensioned such that the slide member and the pusher are distally movable independently of each other; and a clip advancement mechanism and a clip track positioned at least partially within the central body portion, the clip track defining a longitudinal axis and being configured and dimensioned to retain a series of clips therein, each clip in the series of clips being in direct contact with at least one adjacent clip, the clip advancement mechanism further including a clip follower positioned proximally of the series of clips to engage a proximal-most clip of the series of clips such that advancement of the clip follower effectuates advancement of the series of clips, wherein the anvil jaw and the slide member are configured to define an enclosed tissue receiving area when the slide member is in the second position.

21. A clip applying apparatus according to claim 20, wherein the clip track defines a channel dimensioned to slidably receive the series of clips such that the series of clips is movable relative to the clip track through the channel.

22. A clip applying apparatus according to claim 20, wherein the clip track is substantially fixed relative to the central body portion.

23. A clip applying apparatus according to claim 20, wherein the clip track is substantially linear in configuration.

24. A clip applying apparatus according to claim 20, wherein the clip follower includes a tab configured and dimensioned for engagement with the clip track to allow distal movement of the clip follower relative to the clip track and restrict proximal movement of the clip follower relative to the clip track.

25. A clip applying apparatus according to claim 24, wherein the clip track includes at least one opening configured and dimensioned to receive the tab.

26. A clip applying apparatus according to claim 25, wherein the clip track includes a series of openings spaced apart along the longitudinal axis of the clip track.

27. A clip applying apparatus comprising:

a handle assembly;

a central body portion extending distally from the handle assembly;

an anvil jaw supported on a distal end of the central body portion, the anvil jaw being configured to engage a clip;

a slide member movably supported in relation to the anvil jaw for distal movement from a first position to a second position;

a pusher operably associated with the handle assembly, the pusher being distally movable from a retracted position to an advanced position to engage a clip and effectuate deformation of the clip in cooperation with the anvil jaw, wherein the slide member and the pusher are configured and dimensioned such that the slide member and the pusher are distally movable independently of each other, the slide member and the pusher being operatively connected such that movement of the slide member into the second position precedes movement of the pusher into the advanced position; and a clip advancement mechanism and a clip track housing a series of clips, the clip advancement mechanism including a clip follower positioned to engage a proximal-most clip of the series of clips to advance the series of clips, wherein the anvil jaw and the slide member are configured to define an enclosed area that is configured and dimensioned to confine tissue when the slide member is in its second position and the pusher is spaced from the advanced position.

* * * * *